US012773399B2

(12) United States Patent
Kim et al.

(10) Patent No.: US 12,773,399 B2
(45) Date of Patent: Oct. 27, 2026

(54) COMPOSITION FOR PREVENTION OR TREATMENT OF CARDIOVASCULAR AND METABOLIC DISEASE COMPRISING NORANHYDROICARITIN

(71) Applicants: SEOUL NATIONAL UNIVERSITY HOSPITAL, Seoul (KR); KOREA RESEARCH INSTITUTE OF BIOSCIENCE AND BIOTECHNOLOGY, Daejeon (KR)

(72) Inventors: Hyo-Soo Kim, Seoul (KR); Hyun-Duk Jang, Seoul (KR); Kyung Seop Ahn, Daejeon (KR); Sei-Ryang Oh, Daejeon (KR); Ji Won Park, Daejeon (KR); Ok-Kyoung Kwon, Daejeon (KR); Hyung Won Ryu, Daejeon (KR)

(73) Assignees: SEOUL NATIONAL UNIVERSITY HOSPITAL, Seoul (KR); KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 1242 days.

(21) Appl. No.: 17/439,577

(22) PCT Filed: Feb. 26, 2020

(86) PCT No.: PCT/KR2020/002773

§ 371 (c)(1),
(2) Date: Sep. 15, 2021

(87) PCT Pub. No.: WO2020/189911

PCT Pub. Date: Sep. 24, 2020

(65) Prior Publication Data

US 2022/0151979 A1 May 19, 2022

(30) Foreign Application Priority Data

Mar. 15, 2019 (KR) ........................ 10-2019-0029921

(51) Int. Cl.

| | |
|---|---|
| ***A61K 31/352*** | (2006.01) |
| ***A61K 31/22*** | (2006.01) |
| ***A61K 31/366*** | (2006.01) |
| ***A61K 31/40*** | (2006.01) |
| ***A61K 31/405*** | (2006.01) |
| ***A61K 31/47*** | (2006.01) |
| ***A61K 31/505*** | (2006.01) |
| ***A61P 9/10*** | (2006.01) |

(52) U.S. Cl.

CPC ............ *A61K 31/352* (2013.01); *A61K 31/22* (2013.01); *A61K 31/366* (2013.01); *A61K 31/40* (2013.01); *A61K 31/405* (2013.01); *A61K 31/47* (2013.01); *A61K 31/505* (2013.01); *A61P 9/10* (2018.01)

(58) Field of Classification Search

CPC .... A61K 31/352; A61K 31/22; A61K 31/366; A61K 31/40; A61K 31/405; A61K 31/47; A61K 31/505; A61P 9/10

See application file for complete search history.

(56) References Cited

U.S. PATENT DOCUMENTS

| | | | | |
|---|---|---|---|---|
| 2005/0182106 A1* | 8/2005 | Kondo | ............... | A61K 31/4415 514/460 |
| 2008/0241240 A1* | 10/2008 | Kim | ..................... | A61K 9/1652 424/468 |
| 2015/0335685 A1 | 11/2015 | Yoon | | |

FOREIGN PATENT DOCUMENTS

| | | | | | |
|---|---|---|---|---|---|
| KR | 10-2008-0090710 A | | 10/2008 | | |
| KR | 10-2009-0084439 A | | 8/2009 | | |
| KR | 2009084439 A | * | 8/2009 | ........... | A23L 29/035 |
| KR | 10-2015-0064400 A | | 6/2015 | | |
| KR | 10-2016-0083806 A | | 7/2016 | | |
| KR | 10-2018-0041233 A | | 4/2018 | | |

OTHER PUBLICATIONS

Mihaylova, B. et al., "The effects of lowering LDL cholesterol with statin therapy in people at low risk of vascular disease: meta-analysis of individual data from 27 randomised trials," Lancet, 2012, vol. 380, pp. 581-590.

International Search Report issued Jun. 4, 2020, corresponding to International Application No. PCT/KR2020/002773.

* cited by examiner

*Primary Examiner* — Kamal A Saeed
*Assistant Examiner* — Quincy Mckoy
(74) *Attorney, Agent, or Firm* — Hauptman Ham, LLP

(57) ABSTRACT

The present invention relates to a composition for prevention or treatment of cardiovascular and metabolic diseases, containing noranhydroicaritin or a pharmaceutically acceptable salt thereof, and the noranhydroicaritin or pharmaceutically acceptable salt thereof of the present invention is not toxic to cells, is thus safe, inhibits the production of PCSK9, promotes the production of LDLR, and is highly utilizable as a composition for prevention or treatment of cardiovascular and metabolic diseases. The noranhydroicaritin of the present invention can be used in a food composition for prevention or improvement of cardiovascular and metabolic diseases, a functional food composition for prevention or improvement of cardiovascular and metabolic diseases, and a method of preventing or treating cardiovascular and metabolic diseases, which includes administering a composition containing noranhydroicaritin as an active ingredient.

3 Claims, 15 Drawing Sheets

COMPOSITION FOR PREVENTION OR TREATMENT OF CARDIOVASCULAR AND METABOLIC DISEASE COMPRISING NORANHYDROICARITIN

CROSS-REFERENCE TO RELATED APPLICATION

The present application is a national stage filing under 35 U.S.C § 371 of PCT application number PCT/KR2020/002773 filed on Feb. 26, 2020 which is based upon and claims the benefit of priorities to Korean Patent Application No. 10-2019-0029921 filed on Mar. 15, 2019, in the Korean Intellectual Property Office. Both of the aforementioned applications are hereby incorporated by reference in their entireties.

TECHNICAL FIELD

The present invention relates to a composition for prevention or treatment of cardiovascular and metabolic diseases containing noranhydroicaritin, more specifically to a composition for prevention or treatment of cardiovascular and metabolic diseases containing noranhydroicaritin that is not toxic to cells but has an effect of inhibiting the production of proprotein convertase subtilisin/kexin type 9 (PCSK9) and promoting the production of low-density lipoprotein receptor (LDLR). The present invention also relates to a functional food composition for prevention or improvement of cardiovascular and metabolic diseases containing noranhydroicaritin, and a method of preventing or treating cardiovascular and metabolic diseases, which includes administering a composition containing noranhydroicaritin.

BACKGROUND ART

Recent abundance and diversity in diet and changes in lifestyle have tended to cause an imbalance in nutritional intake, and modern mechanized life has led to a lack of exercise. As a result, the forms of disease are also changing to those typical of advanced countries, and accordingly, the morbidity of cardiovascular and metabolic diseases is increasing. Cardiovascular and metabolic diseases refer to diseases caused by an imbalance in the metabolism of carbohydrates, lipids, and the like in vivo, and major cardiovascular and metabolic diseases include cardiovascular disease, dyslipidemia, obesity, diabetes mellitus, and the like.

Cardiovascular disease is a disease occurring in the heart and major arteries and is the leading cause of death worldwide. Major diseases belonging to cardiovascular disease include hypertension, angina, myocardial infarction, arteriosclerosis, atherosclerosis, stroke, arrhythmia, and the like. Risk factors related to cardiovascular disease include age, gender, smoking, lack of exercise, obesity, and the like, but the accumulation of cholesterol by lipoprotein may be considered as a representative cause when the recent westernized diet and rapid changes in lifestyle are taken into account.

Arteriosclerosis is the accumulation of fat and fibrous tissue on the inner wall of the artery, causing narrowing or blockage of the blood vessel wall. Normal activity is not affected when arteriosclerosis is mild, but arteriosclerotic heart disease may occur when more than 50% to 70% of coronary tissue is blocked by arteriosclerosis. In severe cases, the cerebral artery or coronary artery may rupture, and cardiovascular disease such as cerebrovascular disease and heart disease develops in such cases. It is known that cerebral arteriosclerosis causes encephalomalacia, and that coronary atherosclerosis causes angina, myocardial infarction, and the like. This may lead to hypertension, heart disease, and cerebral hemorrhage. Currently, various statin-based drugs, which are HMG-CoA reductase inhibitors, have been developed as therapeutic agents for arteriosclerosis, but there is still a need for the development of more effective therapeutic agents.

Dyslipidemia refers to a state in which total cholesterol, LDL-cholesterol, or triglycerides in the blood are increased, or a state in which HDL-cholesterol is decreased. Specific examples thereof include, but are not limited to, hyperlipidemia, hypercholesterolemia, or hypertriglyceridemia. Dyslipidemia may be caused by genetic factors, obesity, diabetes mellitus, drinking, or the like, but in particular, a diet high in fat may increase blood lipids, and thus dyslipidemia may occur. Recently, as an alternative therapy using active ingredients derived from natural products such as herbal medicines and food, or as a method of preparing various extracts, a samulhwalhyeol-tang composition for hyperlipidemia treatment (Korean Patent Publication No. 2015-0064400) has been developed. However, natural pharmaceutical compositions having superior therapeutic effects and fewer side effects than conventional synthetic pharmaceutical compositions or raw materials thereof have not yet been sufficiently developed.

Obesity is widely known to cause chronic diseases such as fatty liver, hypertension, diabetes mellitus, and cardiovascular disease. According to the 2007 National Health and Nutrition Survey by the Ministry of Health, Welfare and Family Affairs, 31.7% of Korean adults are obese. In addition, 1.7 billion people, corresponding to about 25% of the world's population, are currently overweight (BMI>25), and more than 300 million people in the West, including 120 million people in major countries such as the United States, Europe, and Japan, are classified as obese (BMI>30). As an antiobestic drug sold both at home and abroad, there is Xenical, containing orlistat as its main ingredient, which has been approved by the United States FDA. Xenical, which inhibits the action of lipase, is known to cause side effects in the gastrointestinal system such as fatty stool, gas production, and decreased absorption of fat-soluble vitamins.

Diabetes mellitus is divided into two types: insufficient insulin secretion (type I) and impaired glucose metabolism due to insensitivity to insulin (type II). Type II is much more common, accounting for 90% of all diabetics. Type II diabetes mellitus is non-insulin-dependent diabetes mellitus/NIDDM. PPAR-$\gamma$ activators, GLP-1 derivatives, DPP-IV inhibitors, PTP1B inhibitors, and the like have so far been developed as substances for treating non-insulin-dependent diabetes mellitus. As side effects caused by each of these, toxicity to liver, kidney, muscle, and heart, weight gain, and the like are known.

In summary, it can be said that it is important to lower the blood lipid concentration to eliminate the main causes of cardiovascular and metabolic diseases, and dietary therapy suppressing a high-fat diet, exercise therapy, and drug therapy are recommended as methods of lowering the blood lipid concentration. However, strict management and implementation of dietary therapy or exercise therapy is difficult, and there are often limitations in the effect. As lipid concentration-lowering agents developed so far, drugs that lower cholesterol content, such as bile acid-binding resins, HMG-CoA reductase inhibitors, and neomycin and fibric acid derivatives, and drugs that lower the triglyceride content, such as nicotinic acid and fish oil, are used as therapeutic agents. However, these drugs have side effects such as liver toxicity, gastrointestinal disturbance, and cancer occurrence.

Meanwhile, noranhydroicaritin used in the present invention is a compound having a chemical formula of $C_{20}H_{18}O_6$ and a molecular weight of 354.3629 (Komatsu et al. 1970), and is known as a flavonoid-based compound contained in shrubby *sophora* ([*Sophora flavescens*] Aiton). So far, it is not known that noranhydroicaritin has inhibitory activity in certain diseases, but kaempferol, which is the parent of noranhydroicaritin, is only known to have an allergic asthma suppressing effect and anticancer, anti-inflammatory, and antioxidant effects.

DISCLOSURE

Technical Problem

With this background, the present inventors made intensive research efforts to develop a composition that is derived from a natural product and is thus safe while also having an excellent preventive or therapeutic effect on cardiovascular and metabolic diseases, as a result, they have confirmed that noranhydroicaritin, which is a flavonoid-based compound obtained from shrubby *sophora*, has a preventive or therapeutic effect on cardiovascular and metabolic diseases since noranhydroicaritin inhibits PCSK9 production and promotes LDLR production but does not exhibit cytotoxicity, thereby completing the present invention.

Technical Solution

Each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description below.

Further, those skilled in the art will recognize, or be able to ascertain using no more than routine experimentation, many equivalents to the specific embodiments of the invention described herein. Further, these equivalents should be interpreted to fall within the scope of the present invention.

In addition, throughout this specification, when a part is referred to as "including" an element, it will be understood that other elements may be further included rather than other elements being excluded unless content to the contrary is specially described.

An object of the present invention is to provide a pharmaceutical composition for prevention or treatment of cardiovascular and metabolic diseases, containing noranhydroicaritin or a pharmaceutically acceptable salt thereof as an active ingredient.

Another object of the present invention is to provide a food composition for prevention or improvement of cardiovascular and metabolic diseases, containing noranhydroicaritin or a pharmaceutically acceptable salt thereof as an active ingredient.

Still another object of the present invention is to provide a functional food composition for prevention or improvement of cardiovascular and metabolic diseases, containing noranhydroicaritin or a pharmaceutically acceptable salt thereof as an active ingredient.

Still another object of the present invention is to provide a method of preventing or treating cardiovascular and metabolic diseases, which includes administering a composition containing noranhydroicaritin or a pharmaceutically acceptable salt thereof as an active ingredient.

Advantageous Effects

The noranhydroicaritin of the present invention, which is a component extracted from shrubby *sophora*, has an excellent effect of preventing or treating cardiovascular and metabolic diseases. Specifically, the noranhydroicaritin or pharmaceutically acceptable salt thereof of the present invention is not toxic to cells, is thus safe, inhibits the production of PCSK9, promotes the production of LDLR, and is highly utilizable as a composition for prevention or treatment of cardiovascular and metabolic diseases. The noranhydroicaritin of the present invention can also be used in a food composition for prevention or improvement of cardiovascular and metabolic diseases, a functional food composition for prevention or improvement of cardiovascular and metabolic diseases, and a method of preventing or treating cardiovascular and metabolic diseases, which includes administering a composition containing noranhydroicaritin as an active ingredient.

BEST MODE FOR IMPLEMENTATION OF THE INVENTION

Figure 1:
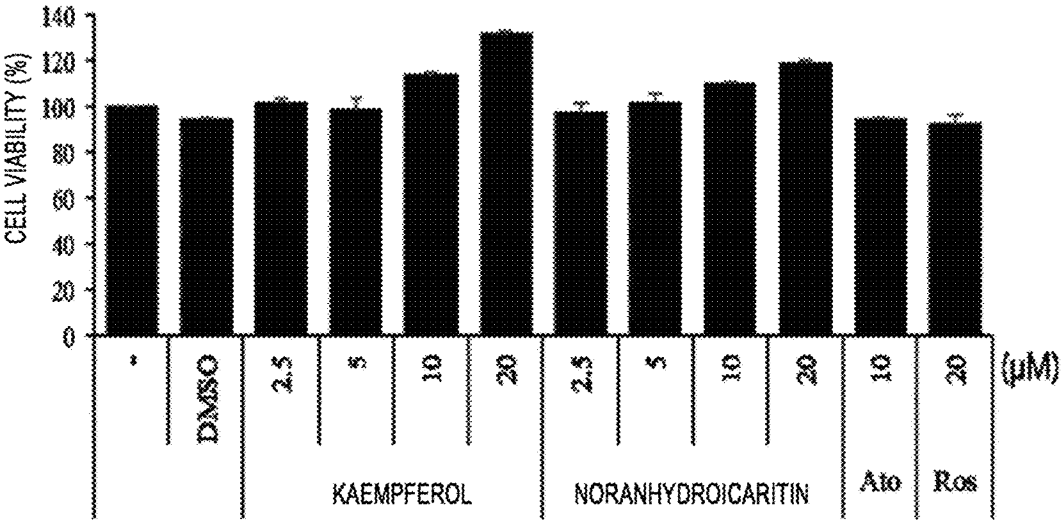
FIG. 1 illustrates the cell viability of HepG2 cells treated with noranhydroicaritin and kaempferol at various concentrations, respectively.

Hereinafter, the present invention will be described in detail.

In order to solve the above problems and achieve the objects of the present invention, the present invention provides a pharmaceutical composition for prevention or treatment of cardiovascular and metabolic diseases, containing noranhydroicaritin or a pharmaceutically acceptable salt thereof as an active ingredient.

As another aspect of the present invention, there is provided the use of noranhydroicaritin or a pharmaceutically acceptable salt thereof for the prevention or treatment of cardiovascular and metabolic diseases.

The "noranhydroicaritin" of the present invention is a compound having a chemical formula of $C_{20}H_{18}O_6$ and a molecular weight of 354.3629 and is a flavonoid-based compound particularly contained in the root of shrubby *sophora* ([*Sophora flavescens*] Aiton). The "flavonoid" is a yellow pigment widely contained in plants, has a carbon skeleton structure in which two phenyl groups are bonded to each other via a 03 chain, and is known as a substance exhibiting various activities in vivo. As used herein, the term "pharmaceutically acceptable" refers to exhibiting non-toxic properties to cells or individuals exposed to the composition, and the term "pharmaceutically acceptable salt" refers to a salt in a form that can be used pharmaceutically among salts, which are substances in which cations and anions are bonded to each other by electrostatic attraction, and may be usually a metal salt, a salt with an organic base, a salt with an inorganic acid, a salt with an organic acid, a salt with a basic or acidic amino acid, and the like.

The "kaempferol" of the present invention is a compound having a chemical formula of $C_{15}H_{10}O_6$ and a molecular weight of 286.24, and belongs to a flavonoid-based compound. In nature, kaempferol is abundantly present after quercetin, and is contained in the form of glycosides in broccoli, grapes, apples, and onions. It is known that kaempferol serves as an antioxidant by decreasing oxidative stress and can diminish the risk of various cancers when ingested (Kim and Choi, 2013).

The "shrubby *sophora* ([*Sophora flavescens*] Aiton)" of the present invention is a perennial plant belonging to the family Fabaceae, the order of Fabales, a dicotyledonous plant, and is also called a thief's stick, Neusam, and snake's shade tree. Shrubby *sophora* is about 80 cm to 120 cm tall and has short yellow hairs all over it, and the root is enlarged and has a greatly bitter taste. In oriental medicine, the dried root of shrubby *sophora* is called Gosam, and is known to be prescribed for indigestion, jaundice, and hemorrhoids. In folklore, the stems or leaves are prepared into a decoction to be used as insecticides.

As used herein, the term "cardiovascular and metabolic diseases" refers to diseases caused by an imbalance in metabolism of carbohydrates, lipids and the like in vivo, and may include, but are not limited to, cardiovascular disease and metabolic disease.

The "cardiovascular disease" is a disease occurring in the heart and major arteries, and the major diseases belonging to cardiovascular disease include hypertension, angina, myocardial infarction, arteriosclerosis, atherosclerosis, stroke, arrhythmia and the like. Accumulation of cholesterol in blood vessels (increase in total cholesterol, LDL cholesterol, triglycerides, and decrease in HDL cholesterol) is one of the main causes of cardiovascular disease.

The "metabolic disease" is not particularly limited, but may include metabolic disease caused by abnormal carbohydrate metabolism or abnormal lipid metabolism. As used herein, specifically the term "metabolic disease caused by abnormal carbohydrate metabolism" refers to a disease caused by an imbalance occurring in the metabolic process of carbohydrates in vivo, and is not particularly limited thereto, but may include diabetes mellitus, prediabetes, type II diabetes mellitus, and the like. Specifically, the term "metabolic disease caused by abnormal lipid metabolism" refers to a disease caused by an imbalance in the metabolic process of lipids in vivo, and is not particularly limited thereto, but may include cardiovascular disease, dyslipidemia, obesity, and the like.

As used herein, the term "toxic" refers to the "adverse effects of chemical, physical or biological substances on living organisms and ecosystems".

As used herein, the term "low-density lipoprotein (LDL)" refers to a product by degradation of very-low-density lipoprotein (VLDL) produced in the liver in blood vessels, and LDL is classified as one of lipoproteins that transport cholesterols in the liver or intestine to tissues. LDL contains apolipoprotein B-100 and Apo E, and antioxidant vitamins such as vitamin E and carotenoids, and synthesizes or stores cell membranes and hormones in tissue cells. LDL binds to the low-density lipoprotein receptor (LDLR) in the cell membrane and is transported into the cell and hydrolyzed in the lysosome, but hypercholesterolemia is caused when the receptor is abnormal. LDL contains a lot of cholesterol, and the risk of coronary artery disease and heart attack may increase when LDL in the blood increases.

As used herein, the term "low-density lipoprotein receptor (LDLR)" refers to a protein, which binds to LDL, which is a major blood cholesterol carrier, and serves to maintain plasma levels of LDL by mediating endocytosis of cholesterol-rich LDL. LDLR is a cell-surface receptor that recognizes apoprotein B100 inserted into the outer phospholipid layer of LDL particles, and endocytosis of LDL through LDLR occurs in all nucleated cells, but mainly the liver clears about 70% of LDL in the blood.

Figure 4:
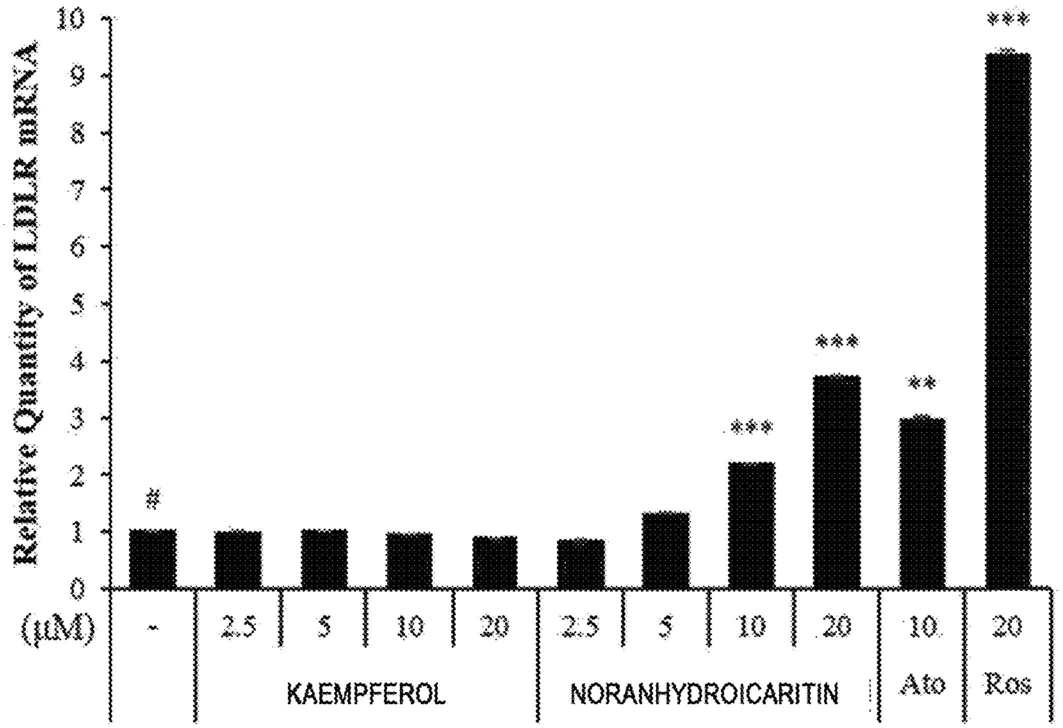
FIG. 4 illustrates the quantity of LDLR mRNA in HepG2 cells treated with noranhydroicaritin and kaempferol at various concentrations, respectively.

In an embodiment of the present invention, in order to confirm the LDLR production increasing effect of noranhydroicaritin, HepG2 cells were treated with noranhydroicaritin at various concentrations, and then the quantity of LDLR mRNA was confirmed through RealTime-PCR (FIG. 4). Through this, it was confirmed that noranhydroicaritin has the effect of increasing LDLR production, can lower blood cholesterol levels, and can thus be used for the prevention or treatment of cardiovascular and metabolic diseases.

As used herein, the term "proprotein convertase subtilisin/kexin type 9 (PCSK9)" of the present invention is an enzyme encoded by the PCSK9 gene on human chromosome 1, and is ubiquitous in a number of tissues and cell types. PCSK9 binds to LDLR, the receptor of LDL, and PCSK9 degrades LDLR to prevent further binding of LDLR to LDL particles and regeneration of LDLR into the cell membrane surface when PCSK9 binds to LDLR after the LDLR-LDL conjugate is absorbed into the cells in the liver and other cell membranes. Therefore, when PCSK9 is blocked or the production of PCSK9 is inhibited, a larger number of LDLRs can be regenerated and the level of LDL particles in the blood can be lowered.

Figure 3:
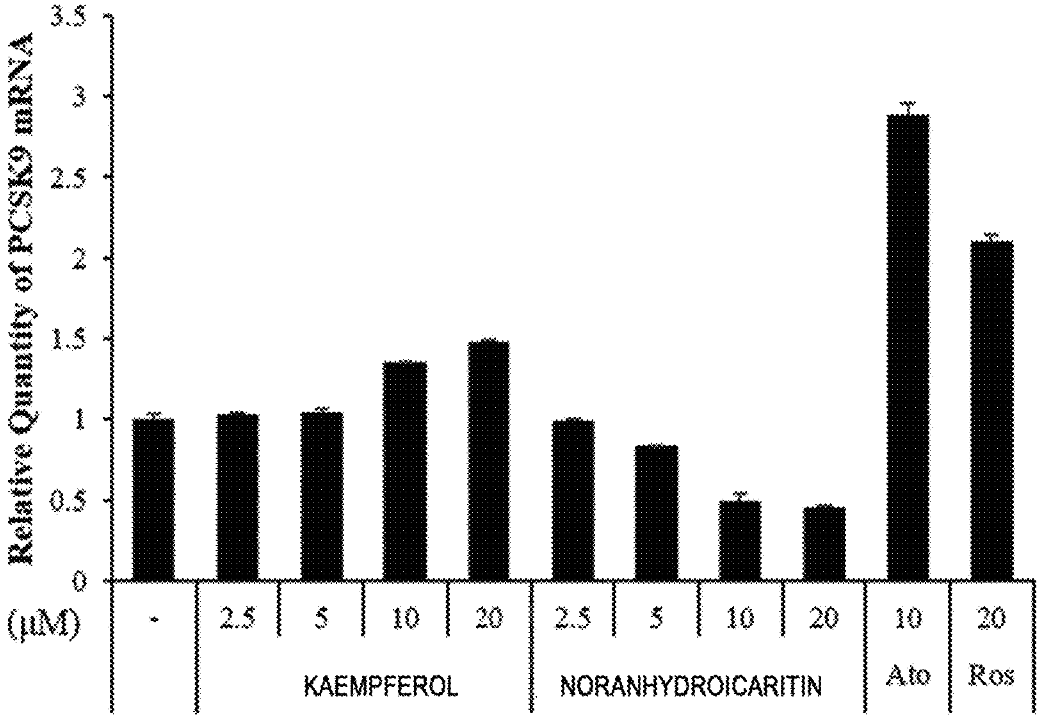
FIG. 3 illustrates the quantity of PCSK9 mRNA in HepG2 cells treated with noranhydroicaritin and kaempferol at various concentrations, respectively.

In an embodiment of the present invention, in order to confirm the PCSK9 production inhibitory effect of noranhydroicaritin, HepG2 cells were treated with noranhydroicaritin at various concentrations, and the quantity of PCSK9 mRNA was confirmed through RealTime-PCR (FIG. 3). Through this, it was confirmed that noranhydroicaritin increases LDLR by inhibiting the production of PCSK9, lowers blood cholesterol levels, and can thus be used for the prevention or treatment of cardiovascular and metabolic diseases.

Figure 5:
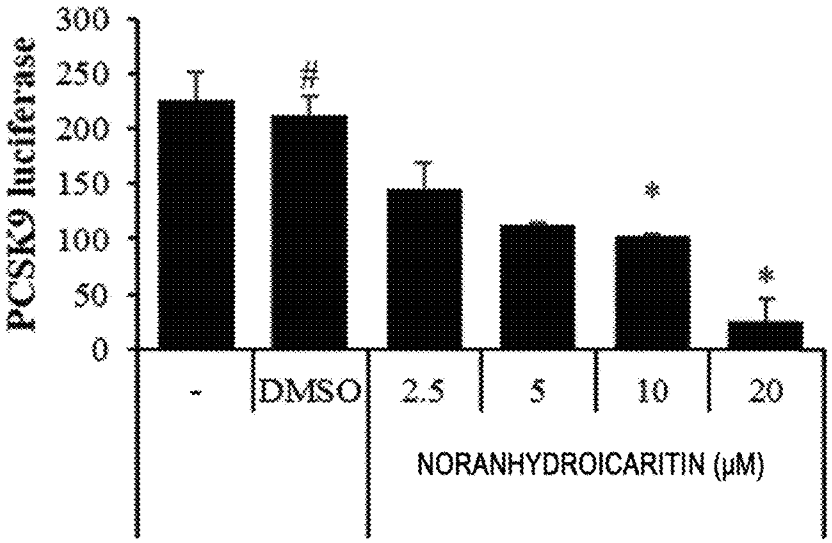
FIG. 5 illustrates the PCSK9 luciferase activity in HEK293T cells that have been transfected with PCSK9 promoter-reporter construct and then treated with noranhydroicaritin at various concentrations.

In an embodiment of the present invention, in order to confirm the effect of inhibiting the expression of PCSK9 gene by the treatment with noranhydroicaritin, the HEK293T cell extract was treated with noranhydroicaritin at various concentrations, and it was confirmed whether the expression of PCSK9 was inhibited through a luciferase assay (FIG. 5). Through this, it was confirmed that noranhydroicaritin increases LDLR by inhibiting the expression of PCSK9 gene, lowers blood cholesterol levels, and can thus be used for the prevention or treatment of cardiovascular and metabolic diseases.

As used herein, the term "AMP-activated protein kinase (AMPK)" refers to an enzyme, which contains a regulatory β/γ subunit and a catalytic a subunit and detects a low energy state by monitoring the ratio of ATP to AMP, and serves to maintain cell energy homeostasis. AMPK is activated (phospho-AMPK, pAMPK) by phosphorylation of threonine 172 by LKB1 and CaMKK ($Ca^{2+}$/calmodulin-dependent kinase kinase), which are upper enzymes of AMPK, during muscle contraction and exercise. In association with the activation of AMPK, effects such as fatty acid oxidation in the liver and skeletal muscle, promotion of glucose uptake, and inhibition of cholesterol synthesis are exhibited. Specifically, glucose uptake in skeletal muscle occurs by enhanced translocation of GLUT4 to the plasma membrane. AMPK is a target molecule of two hormones, leptin and adiponectin, derived from adipose tissue, and these hormones are major regulators of energy metabolism and glucose homeostasis (Ewart and Kennedy, 2012; Penumathsa et al. 2009; Samovski et al. 2012).

As used herein, the term "peroxisome proliferator activated receptor (PPAR)" refers to a transcription factor belonging to the nuclear hormone receptor superfamily which regulates fat metabolism and glucose metabolism and serves to regulate cell proliferation and differentiation. Three types of PPARs of α, β, and γ are known, and these are each expressed by three different genes. While most of the target genes of PPARα are important enzymes that regulate the influx of fatty acids into cells and the oxidation of fat metabolites, PPARγ is expressed in a large quantity in adipose tissue and is known to be involved in the differentiation of adipocytes, storage of excess energy in the form of fat, and regulation of insulin and glucose homeostasis.

Figure 7:
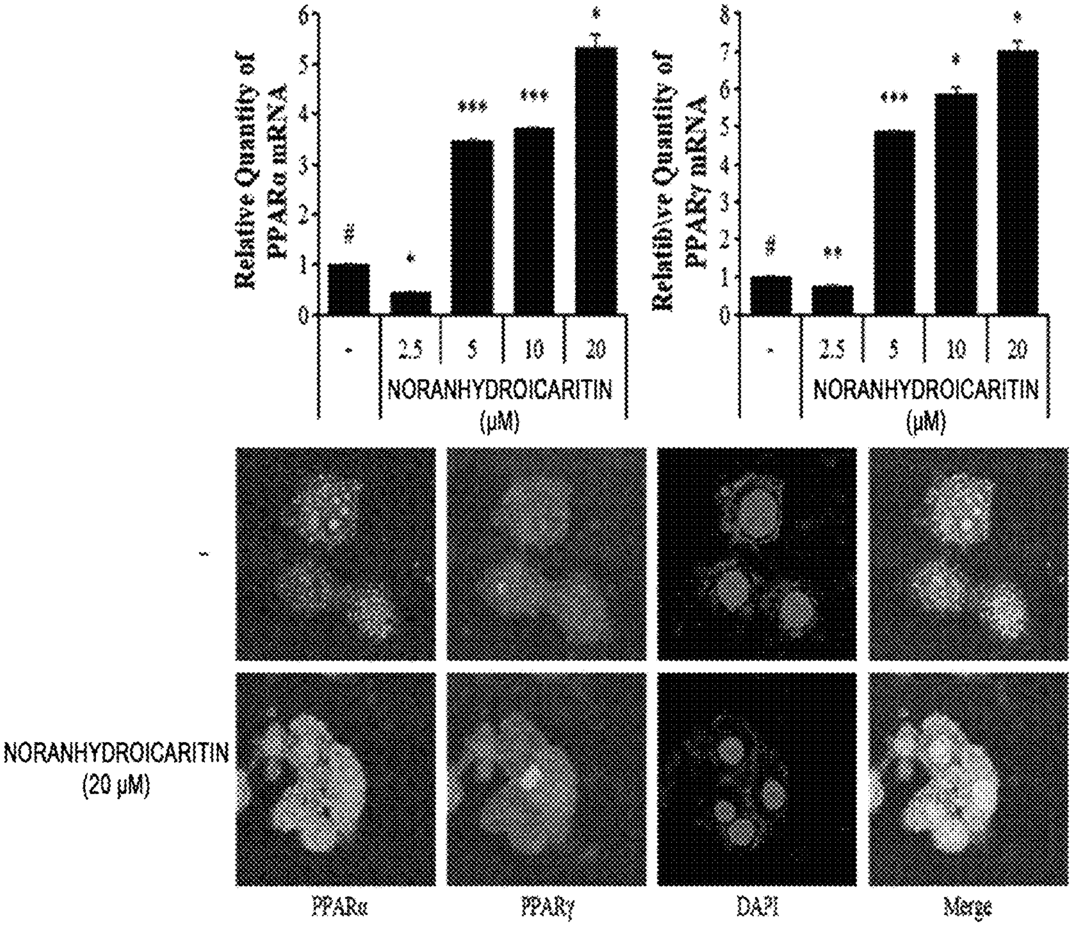
FIG. 7 illustrates the quantities of PPARα mRNA and PPARγ mRNA in HepG2 cells treated with noranhydroicaritin at various concentrations, and the increment in PPARα and PPARγ by immunohistochemistry.

In an embodiment of the present invention, the effect of increasing the expression of PPARα and PPARγ by treatment with noranhydroicaritin was confirmed, and as a result, it was confirmed that the expression of PPARα and PPARγ increases in a concentration-dependent manner in the group treated with noranhydroicaritin (FIG. 7). From this, it was confirmed that noranhydroicaritin increases the expression of PPARα and PPARγ to promote the absorption and catabolism of fatty acids in the blood, and can thus be used for the prevention or treatment of cardiovascular and metabolic diseases.

As used herein, the term "sterolregulatory element binding protein (SREBP)" refers to an important transcriptional activator that regulates fatty acid and cholesterol synthesis in the liver by activating enzymes involved in the biosynthesis pathway of fatty acids and cholesterol. There are three types of SREBPs of 1a, 1c, and 2, SREBP-1a and SREBP-1c are known to be mainly involved in the synthesis of fatty acids and triglycerides, and SREBP-2 is known to be involved in cholesterol metabolism. Hyperinsulinemia caused by insulin resistance increases the expression of SREBP-1c in the liver to increase the biosynthesis of fatty acids and consequently cause the accumulation of triglycerides in the liver tissue. SREBP-1c is a transcription factor that increases the expression of a liposynthesis enzyme, acetyl-CoA carboxylase (ACC), and fatty acid synthase (FAS) genes, and causes fatty acid accumulation in hepatocytes by increasing the expression of ACC and FAS.

Meanwhile, the activity of SREBP-1c is inhibited by the "AMP-activated protein kinase (AMPK)", and AMPK is a type of serine/threonine kinase that is activated when intracellular energy (ATP) is insufficient and increases intracellular energy production. Activated AMPK stimulates catabolism, which produces ATP, such as beta-oxidation of fatty acids, and inhibits processes which consume ATP, such as adipogenesis. Consequently, AMPK activation inhibits liposynthesis by inhibiting the expression of lipase through downregulation of SREBP-1c activity.

Figure 8:
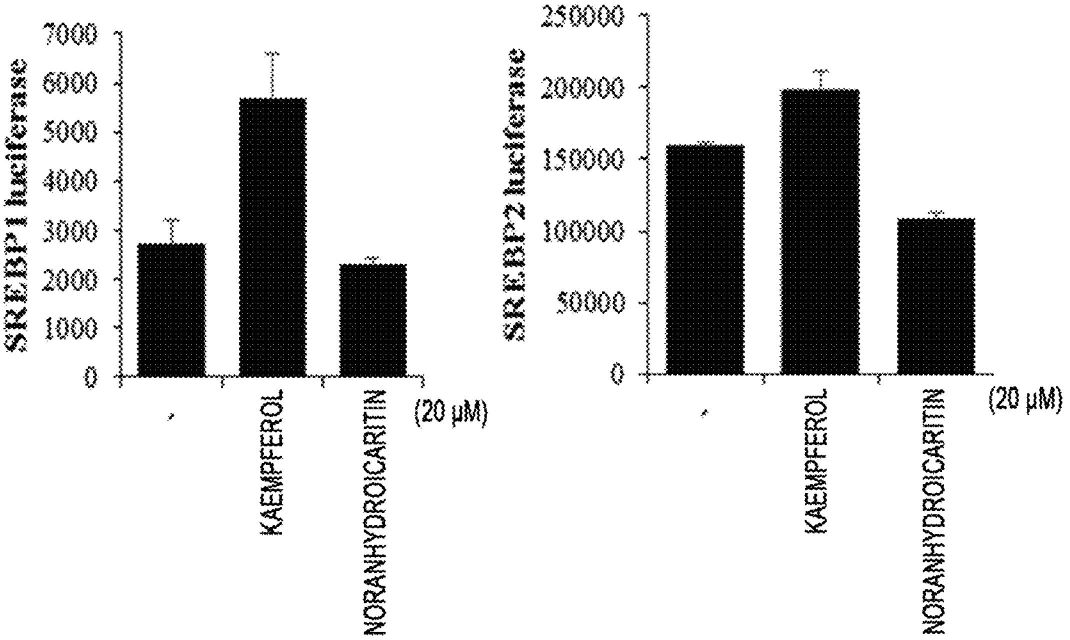
FIG. 8 illustrates the SREBP luciferase activity in HEK293T cells that have been transfected with SREBP promoter-reporter construct and then treated with noranhydroicaritin and kaempferol at various concentrations, respectively.

In an embodiment of the present invention, HEK293T cells were treated with noranhydroicaritin and kaempferol, respectively, and it was confirmed whether the expression of SREBP was inhibited through a luciferase assay. As a result, it was confirmed that SREBP 1 and 2 luciferase activity actually increases in the cells treated with kaempferol as compared to that in the control but SREBP 1 and 2 luciferase activity significantly decreases in the cells treated with noranhydroicaritin as compared to that in the cells treated with kaempferol and that in the control (FIG. 8). From this, it can be seen that noranhydroicaritin down-regulates the expression of SREBP gene to inhibit the synthesis of fatty acids and cholesterol in the liver, and can thus be used for the prevention or treatment of cardiovascular and metabolic diseases.

In the present invention, the pharmaceutical composition may further contain a statin-based drug, but is not limited thereto.

As used herein, the term "statins" refers to a drug that lowers serum cholesterol concentration by acting as a competitive inhibitor of HMG-CoA (3-hydroxy-3-methylglutaryl-coenzyme A) reductase involved in the initial stage of cholesterol biosynthesis, and is used interchangeably with "statin-based drugs" herein. The statins inhibit cholesterol synthesis in hepatocytes and increase low-density lipoprotein receptor (LDLR) expression to lower low-density lipoprotein-cholesterol (LDL-C) levels in the blood. In addition, the statins have the effect of lowering triglyceride levels and increasing high density lipoprotein-cholesterol (HDL-C)

levels, and is thus generally used for lipid control in dyslipidemia patients. In the present invention, the statins may be atorvastatin, rosuvastatin, pitavastatin, pravastatin, simvastatin, or fluvastatin, but is not particularly limited thereto as long as they have HMG-CoA reductase inhibitory activity.

However, side effects of statin-based drugs, which appear in proportion to the effect, include elevated liver somatic index and rhabdomyolysis. Studies on the mechanism show that statin-based drugs increase LDLR but also increase PCSK9 in proportion, and it is thus important to study adjuvant drugs, which can compensate for this. Specifically, the side effect may be a concomitant increase in PCSK9. In particular, when LDL-C of the treatment target is not achieved even with a statin, the amount of statin may be increased to the maximum dose, but combination therapy with other drugs is recommended. The effect of drug can be expected by treating the elderly and severely ill patients with a statin at a high concentration, but side effects may occur in proportion. Therefore, studies on co-administration of adjuvant drugs, which can compensate for this, are in the spotlight. When adjuvant drugs are administered in combination, superior prevention or treatment effects of cardiovascular and metabolic diseases can be expected through the increase in LDLR and the decrease in PCSK9 activity.

In an embodiment of the present invention, the arteriosclerosis-related protein inhibitory effect was confirmed when HepG2 cells were treated with noranhydroicaritin and a statin in combination, and it was confirmed that there was a PCSK9 inhibitory effect when HepG2 cells pre-treated with PCSK9 were treated with noranhydroicaritin and a statin in combination (FIGS. 9 to 12). Therefore, noranhydroicaritin can be used with statin-based drugs in combination to alleviate the side effects of increasing not only LDLR but also PCSK9 at the time of treatment with statin-based drugs. In this case, a synergistic action is acquired such that the expression of pAMPK, LDLR, and PPARγ increases as compared to that in the case of treating the cells with noranhydroicaritin singly. As a result, noranhydroicaritin decreases fatty acids and cholesterol in the blood and can thus be used for the prevention or treatment of cardiovascular and metabolic diseases.

As used herein, the term "pharmaceutical composition" refers to one prepared for the purpose of preventing or treating a disease, and each may be formulated in various forms according to conventional methods and used. For example, the pharmaceutical composition may be formulated in oral dosage forms such as powders, granules, tablets, capsules, suspensions, emulsions, and syrups, and may be formulated in parenteral dosage forms using diluents or excipients such as lubricants, wetting agents, flavoring agents, emulsifying agents, suspending agents, preservatives, and surfactants. In addition, the pharmaceutical composition may be formulated and used in the form of external preparations, suppositories, and sterile injection solutions. In the case of being formulated, preparations are prepared using diluents or excipients such as fillers, extenders, binders, wetting agents, disintegrants, and surfactants, which are commonly used. Specifically, solid preparations for oral administration include tablets, pills, powders, granules, capsules and the like, and these solid preparations may be prepared by mixing the compound with at least one or more excipients, for example, starch, calcium carbonate, sucrose, lactose, and gelatin. In addition to simple excipients, lubricants such as magnesium stearate and talc may also be used. Liquid preparations for oral use include suspensions, internal solutions, emulsions, syrups, and the like, and may contain various excipients, for example, wetting agents, sweeteners, fragrances, and preservatives in addition to water and liquid paraffin, which are commonly used simple diluents. Preparations for parenteral administration include sterile aqueous solutions, non-aqueous solutions, suspensions, emulsions, lyophilized preparations, and suppositories. As non-aqueous solvents and suspending agents, propylene glycol, polyethylene glycol, vegetable oils such as olive oil, injectable esters such as ethyl oleate, and the like may be used. As the base of suppositories, Witepsol, Macrogol, Tween 61, cacao butter, laurin butter, glycerogelatin, and the like may be used.

Depending on the dosage form, each preparation may be prepared to further contain carriers known in the art, for example, pharmaceutically acceptable carriers, such as buffers, analgesic agents, solubilizers, isotonic agents, stabilizers, and bases. The "pharmaceutically acceptable carrier" may mean a carrier, excipient or diluent, which does not inhibit the biological activity and properties of the injected compound without stimulating the living body, and specifically may be a non-naturally occurring carrier. The kind of carrier usable in the present invention is not particularly limited, and any carrier, which is commonly used in the art and pharmaceutically acceptable, may be used. Non-limiting examples of the carrier include saline, sterile water for injection, Ringer's solution, buffered saline, albumin injection solution, dextrose solution, maltodextrin solution, glycerol, ethanol, and the like. These may be used singly or in mixture of two or more.

As another aspect of the present invention, there is provided a food composition for prevention or improvement of cardiovascular and metabolic diseases, containing noranhydroicaritin or a pharmaceutically acceptable salt thereof as an active ingredient.

As still another aspect of the present invention, there is provided a functional food composition for prevention or improvement of cardiovascular and metabolic diseases, containing noranhydroicaritin or a pharmaceutically acceptable salt thereof as an active ingredient. The noranhydroicaritin, pharmaceutically acceptable salt, and cardiovascular and metabolic diseases are as described above.

As used herein, the term "food" includes meat, sausage, bread, chocolate, candy, snacks, confectionery, pizza, ramen, other noodles, gum, dairy products including ice cream, various soups, beverages, tea, drinks, alcoholic beverages, vitamin complexes, functional food, health food, fermented tea, and the like, and includes all foods in a conventional sense.

As used herein, the term "function(al) food" is the same term as food for special health use (FoSHU), and refers to food with high medical and remedial effects processed to efficiently exhibit bioregulatory functions in addition to nutritional supply. Here, "function(al)" refers to obtaining useful effects for health purposes, such as regulation of nutrients or physiological actions with respect to the structure and function of the human body. The food of the present invention may be prepared by a method commonly used in the art, and may be prepared by adding raw materials and ingredients commonly added in the art at the time of preparation. The form of the food may also not be limited as long as it is a form recognized as food. The food composition of the present invention may be prepared in various forms, and does not have side effects that may occur during long-term administration of drugs and has excellent portability since food is used as a raw material unlike general drugs.

The "health food" refers to food having an active health maintenance or promotion effect compared to general food, and the "health supplement food" refers to food for the purpose of health supplementation. In some cases, the terms functional food, health food, and health supplement food are used interchangeably.

Specifically, the functional food is food prepared by adding the composition of the present invention to food materials such as beverages, teas, spices, gum, and confectionery, or encapsulating, powdering, suspending the composition, refers to food, which brings a specific effect on health when ingested, and has an advantage in that there is no side effect that may occur during long-term administration of drugs since food is used as a raw material unlike general drugs.

The food composition may further contain a physiologically acceptable carrier, and the kind of carrier is not particularly limited, and any carrier commonly used in the art may be used.

The food composition may contain additional ingredients, which are commonly used in food compositions to improve odor, taste, vision, and the like. The food composition may contain, for example, vitamins A, C, D, E, B1, B2, B6, and B12, niacin, biotin, folate, and pantothenic acid. The food composition may contain minerals such as zinc (Zn), iron (Fe), calcium (Ca), chromium (Cr), magnesium (Mg), manganese (Mn), and copper (Cu); and amino acids such as lysine, tryptophan, cysteine, and valine.

The food composition may contain food additives such as preservatives (potassium sorbate, sodium benzoate, salicylic acid, sodium dehydroacetate, and the like), disinfectants (bleaching powder and high bleaching powder, sodium hypochlorite, and the like), antioxidants (butylhydroxyanisole (BHA), butylhydroxytoluene (BHT), and the like), colorants (tar pigment and the like), color couplers (sodium nitrite, sodium nitrite and the like), bleaching agents (sodium sulfite), seasonings (MSG sodium glutamate and the like), sweeteners (dulcin, sodium cyclamate, saccharin, and the like), fragrances (vanillin, lactones, and the like), swelling agents (alum, D-potassium hydrogen tartrate, and the like), strengthening agents, emulsifying agents, thickeners (thickening agents), coating agents, gum bases, defoamers, solvents, and improving agents. The additives may be selected depending on the kind of food and used in appropriate amounts.

As an example, the food composition of the present invention may be used as a health beverage composition, and in this case, the health beverage composition may contain various flavoring agents or natural carbohydrates as additional ingredients like a conventional beverage. The natural carbohydrates may be monosaccharides such as glucose and fructose; disaccharides such as maltose and sucrose; polysaccharides such as dextrin and cyclodextrin; sugar alcohols such as xylitol, sorbitol, and erythritol. As sweeteners, natural sweeteners such as thaumatin, *stevia* extract; synthetic sweeteners such as saccharin and aspartame; and the like may be used. The ratio of the natural carbohydrate may be generally about 0.01 g to 0.04 g, specifically about 0.02 g to 0.03 g per 100 mL of the health beverage composition of the present invention.

In addition to the above, the health beverage composition may contain various nutrients, vitamins, electrolytes, flavor modifiers, colorants, pectic acid, salts of pectic acid, alginic acid, salts of alginic acid, organic acids, protective colloidal thickeners, pH adjusters, stabilizers, preservatives, glycerin, alcohols or carbonating agents. In addition to these, the health beverage composition may contain pulp for the preparation of natural fruit juice, fruit juice beverage, or vegetable beverage. These ingredients may be used independently or in mixture. The ratio of these additives is not greatly important, but is generally selected in a range of 0.01 to 0.1 parts by weight per 100 parts by weight of the health beverage composition of the present invention.

As still another aspect of the present invention, there is provided a method of preventing or treating cardiovascular and metabolic diseases, which includes administering a pharmaceutical composition containing noranhydroicaritin or a pharmaceutically acceptable salt thereof as an active ingredient. The noranhydroicaritin, pharmaceutically acceptable salt, and cardiovascular and metabolic diseases are as described above.

As used herein, the term "prevention" refers to any action in which a composition is administered to suppress or delay the onset of cardiovascular and metabolic diseases. For the purpose of the present invention, the prevention may be understood as an action in which the pharmaceutical composition of the present invention is used to suppress or delay the onset of cardiovascular and metabolic diseases, but is not particularly limited thereto.

As used herein, the term "improvement" refers to any action to at least diminish the degree of cardiovascular and metabolic diseases.

As used herein, the term "treatment" refers to any action in which a pharmaceutical composition is administered to improve or beneficially change symptoms caused by cardiovascular and metabolic diseases. For the purpose of the present invention, the treatment may be understood as an action in which the pharmaceutical composition of the present invention is used to improve the symptoms of cardiovascular and metabolic disease or alleviate the pathological symptoms, but is not particularly limited thereto.

The "individual" refers to any animal, including humans, which has or may develop cardiovascular and metabolic diseases.

As used herein, the term "administration" refers to introduction of the pharmaceutical composition of the present invention to an individual or treatment of an individual with the pharmaceutical composition in an appropriate way. Specifically, administration may be to administer noranhydroicaritin and a statin-based drug in combination by using the pharmaceutical composition of the present invention. The statin-based drug may be atorvastatin or rosuvastatin, but is not limited thereto. The noranhydroicaritin and statin-based drug may be administered in combination to an individual simultaneously, sequentially, or in reverse order.

The pharmaceutical composition of the present invention may be administered in a pharmaceutically effective amount, the pharmaceutically effective amount refers to an amount sufficient to treat a disease at a reasonable benefit/risk ratio applicable to medical treatment and not to cause side effects, and can be easily determined by those skilled in the art according to factors well known in the medical field. The route and mode of administering the pharmaceutical composition of the present invention are not particularly limited, and arbitrary route and mode of administration by which the composition can reach an individual may be adopted in order to achieve the object of the present invention.

The pharmaceutical composition provided in the present invention contains noranhydroicaritin or a pharmaceutically acceptable salt thereof as an active ingredient, is not toxic to cells, and has an effect of inhibiting PCSK9 production and PCSK9 gene expression and generating LDLR.

In an embodiment of the present invention, HepG2 cells were treated with noranhydroicaritin at various concentrations, and then the quantity of LDLR mRNA was confirmed through RealTime-PCR (FIG. 4). As a result, it was confirmed that noranhydroicaritin has an effect of increasing LDLR production, can lower blood cholesterol levels, and can thus be used for the prevention or treatment of cardiovascular and metabolic diseases.

In an embodiment of the present invention, HepG2 cells were treated with noranhydroicaritin at various concentrations, and then the quantity of PCSK9 mRNA was confirmed through RealTime-PCR (FIG. 3). As a result, it was confirmed that noranhydroicaritin increases LDLR by inhibiting the production of PCSK9, lowers blood cholesterol levels, and can thus be used for the prevention or treatment of cardiovascular and metabolic diseases.

In an embodiment of the present invention, PCSK9 promoter-reporter construct-transfected HEK293T cells were treated with noranhydroicaritin at various concentrations, and it was confirmed whether the expression of PCSK9 was inhibited through a luciferase assay (FIG. 5). As a result, it was confirmed that noranhydroicaritin increases LDLR by inhibiting the expression of PCSK9 gene, lowers blood cholesterol levels, and can thus be used for the prevention or treatment of cardiovascular and metabolic diseases.

The pharmaceutical composition may further contain suitable carriers, excipients, and diluents, which are commonly used in the preparation of pharmaceutical compositions. The carriers, excipients, and diluents include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

The pharmaceutical composition of the present invention may be formulated and used in oral dosage forms such as powders, granules, tablets, capsules, suspensions, emulsions, syrups, and aerosols and in the form of external preparations, suppositories and sterile injection solutions according to conventional methods, respectively. In the case of being formulated, preparations are prepared using diluents or excipients, such as fillers, extenders, binders, wetting agents, disintegrants, and surfactants, which are commonly used. Solid preparations for oral administration include tablets, pills, powders, granules, capsules and the like, and these solid preparations are prepared by mixing the extract of the mixture with at least one or more excipients, for example, starch, calcium carbonate, sucrose or lactose, and gelatin. In addition to simple excipients, lubricants such as magnesium stearate and talc may also be used. Liquid preparations for oral use include suspensions, internal solutions, emulsions, syrups, and the like, and may contain various excipients, for example, wetting agents, sweeteners, fragrances, and preservatives in addition to water and liquid paraffin, which are commonly used simple diluents. Preparations for parenteral administration include sterile aqueous solutions, non-aqueous solutions, suspensions, emulsions, lyophilized preparations, and suppositories. As non-aqueous solvents and suspending agents, propylene glycol, polyethylene glycol, vegetable oils such as olive oil, injectable esters such as ethyl oleate, and the like may be used. As the base of suppositories, Witepsol, Macrogol, Tween 61, cacao butter, laurin butter, glycerogelatin, and the like may be used.

As still another aspect of the present invention, there is provided an adjuvant for alleviation of side effects of statin-based drugs, containing noranhydroicaritin or a pharmaceutically acceptable salt thereof as an active ingredient.

As still another aspect of the present invention, there is provided the use of noranhydroicaritin or a pharmaceutically acceptable salt thereof for alleviation of the side effects of statin-based drugs.

The noranhydroicaritin, pharmaceutically acceptable salt, and statin-based drugs are as described above.

The "adjuvant" refers to a substance that can be administered with a statin-based drug in combination to alleviate the side effects of the statin-based drug and thus to enhance the effect of preventing or treating cardiovascular and metabolic diseases, but is not limited thereto. Statin-based drugs have the side effect of not only increasing the expression of LDLR but also increasing PCSK9 in proportion. Therefore, in order to compensate for this, by administering noranhydroicaritin as an adjuvant in combination, the effect of increasing LDLR and the effect of decreasing PCSK9 may be achieved at the same time, and a superior effect of preventing or treating cardiovascular and metabolic diseases may be expected.

As still another aspect of the present invention, there is provided a method of alleviating a side effect of a statin-based drug, which includes administering noranhydroicaritin and a statin-based drug in combination. The noranhydroicaritin, pharmaceutically acceptable salt, statin-based drug, individual, and administration are as described above.

DETAILED DESCRIPTION OF THE INVENTION

Hereinafter, the configuration and effects of the present invention will be described in more detail with reference to Examples. However, these Examples are for illustrative purposes only, and the scope of the present invention is not intended to be limited by these Examples.

Example 1: Isolation of Noranhydroicaritin from Shrubby *Sophora* Extract

Dried root of shrubby *sophora* (203 g) was finely ground, and 100% methanol (MeOH, 1 L×3) was added thereto, followed by extraction at room temperature for 24 hours three times, and filtration. The obtained filtrate was concentrated under reduced pressure to obtain a MeOH extract (13.9 g, extraction yield 6.8%). In a column tube filled with YMC ODS AQ HG (220 g) in a 250 mm×20 mm MPLC instrument, 1.0 g of the obtained extract was placed to obtain a total of nine fractions (SF Fr. 1 to 9) under reverse-phase conditions (0-15 min 35% MeOH, 15-65 min 35-100% MeOH, 65-90 min 100% MeOH) using a UV detector (254 nm). It was confirmed through UPLC-QTof-MS analysis that the fraction SF Fr. 7 contained noranhydroicaritin, this fraction SF Fr. 7 was concentrated, and noranhydroicaritin was isolated via column chromatography using a reversed-phase column (YMC ODS AQ, 250 mm×20 mm, 5 μm, Japan) in PLC2020 prep-HPLC (YMC, Japan) and a mixed solvent of distilled water (A) and MeOH (B) as a mobile phase under conditions of 0-5 min 30% (B), 5-35 min 60% (B), 35-40 min 100% (B). The isolated noranhydroicaritin had a retention time of 5.75 min in UPLC analysis, UV at 224 nm and 271 nm, high-resolution electron spray ionization mass spectrometry (HRESIMS) value of 353.1055 $[M-H]^-$, and a molecular formula of $C_{20}H_{18}O_6$.

Example 2: Cell Viability of HepG2 Cells Treated with Noranhydroicaritin

In order to confirm the toxicity of noranhydroicaritin to cells, HepG2 cells (human liver hepatocellular carcinoma)

were treated with each of kaempferol and noranhydroicaritin at various concentrations, and the cell viability of HepG2 cells at each concentration was calculated through the MTT screening method.

Specifically, HepG2 cells were suspended in DMEM (Welgene Inc.) medium containing 10% fetal bovine serum at a concentration of $1\times10^5$ cells/mL, and 100 μL thereof was inoculated into each well of a 96-well plate. After 4 hours, the HepG2 cells in the well plate were treated with each of kaempferol and noranhydroicaritin samples at concentrations of 2.5 μM, 5 μM, 10 μM, and 20 μM. After incubation for 24 hours, 5 μL of MTT (5 mg/mL) was added to the well plate, and the cells were further incubated for 4 hours. Thereafter, the medium was removed, 100 μL of DMSO was added to the well plate, the reaction was conducted, and then the absorbance was measured at 570 nm. As a control, cholesterol synthesis inhibitors atorvastatin (Ato) and rosuvastatin (Ros) were used. The cell viability was calculated according to the following mathematical formula as a value relative to 100% of the value for the negative control treated only with DMSO. The results are illustrated in FIG. 1.

Cell viability=[(value for sample treated with extract at OD570 nm)/(value for negative control at OD570 nm)]×100 [Math. 1]

As can be seen from FIG. 1, the cell viability of the cells treated with noranhydroicaritin was higher than the cell viability of the cells treated with atorvastatin or rosuvastatin as a control at the same concentration. In particular, the cell viability of the cells treated with noranhydroicaritin was as high as 90% or more even at the highest concentration of 20 μM. Through this, it was confirmed that noranhydroicaritin exhibits low cytotoxicity and is thus safe as a composition for the prevention or treatment of cardiovascular and metabolic diseases.

Example 3: Cell Viability of HEK293T Cells Treated with Noranhydroicaritin

In order to confirm the toxicity of noranhydroicaritin to cells, HEK293T (human embryonic kidneys) were treated with noranhydroicaritin at various concentrations, and the cell viability at each concentration of noranhydroicaritin was calculated through the MTT screening method.

Specifically, HEK293T cells were suspended in DMEM (Welgene Inc.) medium containing 10% fetal bovine serum at a concentration of $1\times10^5$ cells/mL, and 100 μL thereof was inoculated into each well of a 96-well plate. After 4 hours, the HEK293T cells in the well plate were treated with noranhydroicaritin samples at concentrations of 2.5 μM, 5 μM, 10 μM, and 20 μM. After incubation for 24 hours, 5 μL of MTT (5 mg/mL) was added to the well plate, and the cells were further incubated for 4 hours. Thereafter, the medium was removed, 100 μL of DMSO was added to the well plate, the reaction was conducted, and then the absorbance was measured at 570 nm. As a control, cholesterol synthesis inhibitors atorvastatin (Ato) and rosuvastatin (Ros) were used. The cell viability was calculated according to the mathematical formula as a value relative to 100% of the value for the negative control treated only with DMSO. The results are illustrated in FIG. 2.

Figure 2:
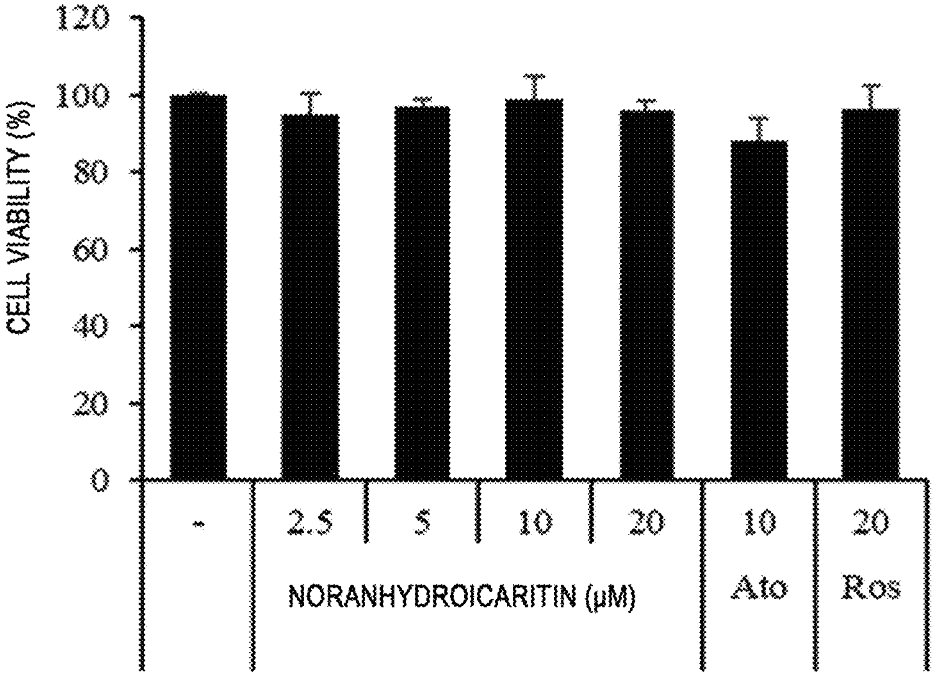
FIG. 2 illustrates the cell viability of HEK293T cells treated with noranhydroicaritin at various concentrations.

As can be seen from FIG. 2, the cell viability of the cells treated with noranhydroicaritin was similar to or higher than the cell viability of the cells treated with atorvastatin or rosuvastatin as a control at the same concentration. The cell viability of the cells treated with noranhydroicaritin was as high as 90% or more even at the highest concentration of 20 μM. Through this, it was confirmed that noranhydroicaritin exhibits low cytotoxicity and is thus safe as a composition for the prevention or treatment of cardiovascular and metabolic diseases.

Example 4: PCSK9 Production Inhibitory Effect of Noranhydroicaritin in HepG2 Cells Proprotein convertase subtilisin/kexin type 9 (PCSK9) is an enzyme involved in lipid metabolism and is attached to low-density lipoprotein receptor (LDLR) bound to low-density lipoprotein (LDL) in the liver or other cell membranes to degrade LDLR so that LDLR cannot be regenerated into the cell membrane and cannot absorb extracellular LDL. Therefore, inhibition of PCSK9 production increases LDLR, decreases extracellular LDL, and lowers cholesterol levels, and thus lipid metabolism-related diseases may be alleviated. Therefore, in order to confirm the PCSK9 production inhibitory effect of noranhydroicaritin, HepG2 cells were treated with noranhydroicaritin at various concentrations, and then the relative quantity of PCSK9 mRAN was confirmed through RealTime-PCR.

Specifically, HepG2 cells were suspended at a concentration of $2.5\times10^5$ cells/mL, and 1 mL thereof was inoculated into each well of a 23-well plate, and then maintained for one day. The HepG2 cells in the well plate were treated with kaempferol and noranhydroicaritin at concentrations of 2.5 μM, 5 μM, 10 μM, and 20 μM, and incubated for 24 hours, and then RNA was recovered, quantified, and stored at −70° C. Thereafter, cDNA was synthesized from the RNA and the quantity of PCSK9 mRNA was confirmed through Real-Time-PCR analysis. The group treated only with DMSO was used as a negative control. The results are illustrated in FIG. 3.

As can be seen from FIG. 3, noranhydroicaritin exhibited a PCSK9 production inhibitory effect superior to that of atorvastatin or rosuvastatin as a control at the same concentration. In particular, even at low concentrations of 2.5 μM and 5 μM, noranhydroicaritin exhibited a PCSK9 production inhibitory effect remarkably superior to that of the control. Through this, it was confirmed that noranhydroicaritin increases LDLR by inhibiting the production of PCSK9, lowers blood cholesterol levels, and can thus be used for the prevention or treatment of cardiovascular and metabolic diseases.

Example 5: LDLR Production Increasing Effect of Noranhydroicaritin in HepG2 Cells LDLR is a protein binding to LDL, a carrier of blood cholesterol, can lower blood cholesterol levels by binding to LDL and absorbing LDL into cells, and thus can alleviate cardiovascular and metabolic diseases. Therefore, in order to confirm the LDLR production increasing effect of noranhydroicaritin, HepG2 cells were treated with noranhydroicaritin at various concentrations, and then the relative quantity of LDLR mRNA was confirmed through RealTime-PCR.

Specifically, HepG2 cells were suspended at a concentration of $2.5\times10^5$ cells/mL, and 1 mL thereof was inoculated into each well of a 23-well plate, and then maintained for one day. The HepG2 cells in the well plate were treated with kaempferol and noranhydroicaritin at concentrations of 2.5 μM, 5 μM, 10 μM, and 20 μM, and incubated for 24 hours, and then RNA was recovered, quantified, and stored at −70° C. Thereafter, cDNA was synthesized from the RNA and the quantity of LDLR mRNA was confirmed through RealTime- PCR analysis. The group treated only with DMSO was used as a negative control. The results are illustrated in FIG. 4.

As can be seen from FIG. 4, noranhydroicaritin exhibited an LDLR production increasing effect similar to or higher than that of the parent kaempferol at all concentrations, and exhibited an LDLR production increasing effect similar to that of atorvastatin as a control at 10 μM. Through this, it was confirmed that noranhydroicaritin has an LDLR production increasing effect, can lower blood cholesterol levels, and can thus be used for the prevention or treatment of cardiovascular and metabolic diseases.

Example 6: PCSK9 Gene Expression Inhibitory Effect by Treatment of PCSK9 Promoter-Reporter Construct-Transfected HEK293T Cells with Noranhydroicaritin In order to confirm the PCSK9 gene expression inhibitory effect of noranhydroicaritin, HEK293T cells were treated with noranhydroicaritin at various concentrations, and it was confirmed whether the expression of PCSK9 was inhibited through a luciferase assay.

i) A primer was prepared to contain KpnI and XhoI restriction enzyme sites in the PCSK9 promoter gene region, and then PCR (polymerase chain reaction) and electrophoresis on an agarose gel were performed to isolate PCSK9 promoter region DNA. A pGL4.14-[luc2/Hygro] vector containing a firefly luciferase as a reporter gene was treated with the same restriction enzymes (KpnI and XhoI), and then isolated via agarose gel electrophoresis and gel extraction. The purely isolated PCSK9 promoter gene region and pGL4.14-[luc2/Hygro] vector were reacted at 50° C. for 1 hour using In-fusion DNA ligase (Takara), and then transformed into *E. coli* to prepare a promoter-reporter construct in which the PCSK9 promoter was inserted, and this was named pGL4.14-PCSK9.

ii) In order to measure the transcriptional activity of the PCSK9 promoter gene, HEK293T cells were transfected with pGL4.14-PCSK9, and then the luciferase activity of the cell extract was measured. The DNA-lipofectamine complex was prepared according to the manufacturer's protocol using 0.1 μg of promoter-reporter construct and lipofectamine 2000 reagent (Invitrogen). In the process of preparing the DNA-lipofectamine 2000 complex, opti-MEM medium (Invitrogen) was used. 1 mL of HEK293T cells was prepared at a concentration of $2.5\times10^5$ cells/mL in each well of a 12-well plate by checking the number of cells immediately before the addition of DNA. The DNA-lipofectamine complex was carefully mixed with the HEK 293T cells and reacted in an incubator at 37° C. for 6 hours. Thereafter, the medium was changed to find the transfected cells, and the PCSK9-transfected HEK293T cells were found through the luciferase test. After the reaction was completed, the HEK293T cells were treated with noranhydroicaritin at concentrations of 2.5 μM, 5 μM, 10 μM, and 20 μM according to the experimental group, and then incubated for 18 hours.

iii) After 18 hours of incubation, cells were washed with PBS one time, an appropriate amount of luciferase reagent was added to each well, then the plate was shaken for 15 min, the supernatant was obtained, and the transcriptional activity was measured. Passive lysis buffer was used, and the luciferase activity was measured using a microplate luminometer (Tecan). All experiments were performed three times in duplicate. The promoter transcriptional activity was expressed by correcting the transcriptional activity relative to that of the control by the transfection efficiency, and student's t-test was used for statistical processing. The results are illustrated in FIG. 5.

As can be seen from FIG. 5, the decrease in PCSK9 luciferase activity in the cells treated with noranhydroicaritin was greater than that in the control even at a low concentration, and the PCSK9 luciferase activity decreased in a noranhydroicaritin concentration-dependent manner, and it was thus confirmed that the expression of PCSK9 gene would also decrease in proportion to the concentration of noranhydroicaritin. Through this, it was confirmed that noranhydroicaritin increases LDLR by inhibiting the expression of PCSK9 gene, lowers blood cholesterol levels, and can thus be used for the prevention or treatment of cardiovascular and metabolic diseases.

Example 7: Immunoblot Analysis

In order to confirm the effect of noranhydroicaritin to inhibit PCSK9 expression and increase LDLR expression, immunoblotting targeting PCSK9 and LDLR was performed and the expression levels were compared. β-Actin was used as a control.

In a 100 mm Petri dish, $1\times10^6$ HepG2 cells were aliquoted and treated with noranhydroicaritin at various concentrations (5 μM, 10 μM, and 20 μM), and then the cells were removed from the cell-culture dish and homogenized using a protein extraction solution (NP40, ELPIS BIOTECH, Korea) containing a protease inhibitor cocktail (Roche).

In order to prepare the total protein, the cells were extracted in RIPA lysis buffer (50 mM Tris-HCl (pH 7.4), 150 mM NaCl, 5 mM EDTA, 5 mM EGTA, 5 mM sodium fluoride, 2 mM sodium orthovanadate, 1% NP-40, 0.1% sodium dodecyl sulfate [SDS], 1 mM phenylmethylsulfonyl fluoride [PMSF], and protein inhibitor cocktail [Roche Diagnostics, Heidelberg, Germany]). The protein concentration in the lysate was measured using the Bio-Rad dye-binding micro assay. For immunoblotting, 30 μg of cell lysate was isolated via SDS-polyacrylamide gel electrophoresis (PAGE). The proteins were transferred onto the Hybond-ECL nitrocellulose membrane (Amersham Biosciences, Buckinghamshire, UK). The membrane was blocked with TBS (10 mM Tris-HCl pH 7.4, 150 mM NaCl) containing 0.1% Tween 20 and 5% skim milk powder, and the cells were incubated with primary antibodies diluted in blocking buffer; anti-PCSK9 (sc-515082, Santa Cruz), anti-LDLR (sc-18823, Santa Cruz), and anti-β-actin (#4967, cell signaling) overnight in 4. The membrane was washed, and the cells were incubated with appropriate secondary antibodies, goat-anti-rabbit IgG(H+L) (Jackson; 111-035-003) and goat-anti-mouse IgG(H+L) (sc-2005, Santa Cruz), at room temperature for 1 hour. HRP-conjugated secondary antibodies were detected using an ECL detection reagent.

Figure 6:
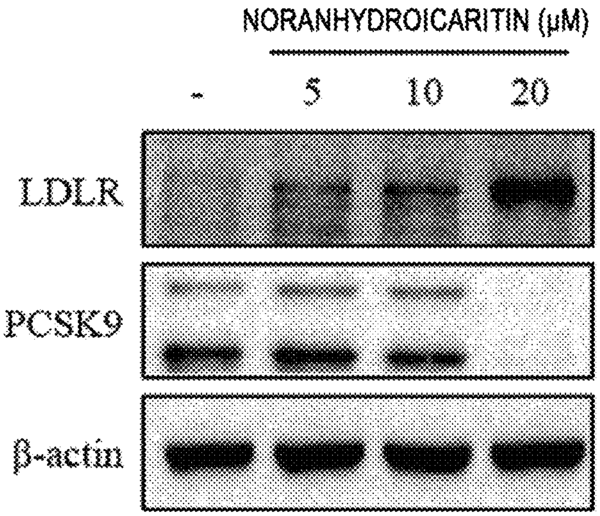
FIG. 6 illustrates the results acquired by performing immunoblotting targeting PCSK9 and LDLR and comparing the expression levels.

As can be seen from FIG. 6, it was confirmed that PCSK9 expression decreased in a concentration-dependent manner and LDLR expression increased in a concentration-dependent manner in cells treated with noranhydroicaritin. Through this, it was confirmed that noranhydroicaritin increases LDLR by inhibiting the expression of PCSK9, lowers blood cholesterol levels, and can thus be used for the prevention or treatment of cardiovascular and metabolic diseases.

Example 8: PPAR Production Effect of Noranhydroicaritin in HepG2 Cells

In order to confirm the effect of increasing the expression of PPARα and PPARγ of noranhydroicaritin, PCR using PPARα primers and immunohistochemistry targeting PPARα and PPARγ were performed to confirm the expression levels.

Using cDNA synthesized with RNA according to the method of Example 4, the quantities of PPARα mRNA and PPARγ mRNA were confirmed through RealTime-PCR analysis. The group treated only with DMSO was used as a negative control. For immunohistochemistry, HepG2 cells were attached to a slide chamber, then treated with noranhydroicaritin at 20 μM, and incubated. After fixation with formalin, the HepG2 cells were stained with antibodies targeting PPARα and PPARγ, and treated with DAPI to stain nuclei, and the degree of fluorescent expression was confirmed using a confocal microscope.

As can be seen from FIG. 7, it was confirmed that the expression of PPARα and PPARγ increased in a concentration-dependent manner in the group treated with noranhydroicaritin. In other words, through this, it was confirmed that noranhydroicaritin increases the expression of PPARα and PPARγ to promote the absorption and catabolism of fatty acids in the blood, and can thus be used for the prevention or treatment of cardiovascular and metabolic diseases.

Example 9: SREBP Gene Expression Inhibitory Effect by Treatment of SREBP Promoter-Reporter Construct-Transfected HEK293T Cells with Noranhydroicaritin In order to confirm the SREBP gene expression inhibitory effect of noranhydroicaritin, HEK293T cells were treated with noranhydroicaritin and kaempferol, and it was confirmed whether the expression of SREBP was inhibited through a luciferase assay.

i) A primer was prepared to contain KpnI and XhoI restriction enzyme sites in the SREBP 1 and 2 promoter gene region, and then PCR (polymerase chain reaction) and electrophoresis on an agarose gel were performed to isolate SREBP promoter region DNA. A pGL4.14-[luc2/Hygro] vector containing a firefly luciferase as a reporter gene was treated with the same restriction enzymes (KpnI and XhoI), and then isolated via agarose gel electrophoresis and gel extraction. The purely isolated SREBP promoter gene region and pGL4.14-[luc2/Hygro] vector were reacted for 1 hour using In-fusion DNA ligase (Takara), and then transformed into *E. coli* to prepare a promoter-reporter construct in which the SREBP promoter was inserted, and this was named pGL4.14-SREBP.

ii) In order to measure the transcriptional activity of the SREBP promoter gene, HEK293T cells were transfected with pGL4.14-SREBP, and then the luciferase activity of the cell extract was measured. HEK293T cells were transfected with the DNA-lipofectamine complex in the same manner as in Example 6, and the SREBP-transfected HEK293T cells were found through a luciferase test. After the reaction, HEK293T cells were divided into a group to be treated with a sample and a group not to be treated with a sample according to the experimental group, treated with the sample, and then incubated for 18 hours. Thereafter, the luciferase activity was measured by the method of Example 6. All experiments were performed three times in duplicate. The promoter transcriptional activity was expressed by correcting the transcriptional activity relative to that of the control by the transfection efficiency, and student's t-test was used for statistical processing.

As can be seen from FIG. 8, it was confirmed that SREBP 1 and 2 luciferase activity actually increased in the cells treated with kaempferol as compared to that in the control but SREBP 1 and 2 luciferase activity significantly decreased in the cells treated with noranhydroicaritin as compared to that in the cells treated with kaempferol and that in the control. From this, it was confirmed that noranhydroicaritin down-regulates the expression of SREBP gene to inhibit the synthesis of fatty acids and cholesterol in the liver, and can thus be used for the prevention or treatment of cardiovascular and metabolic diseases.

Example 10: Arteriosclerosis-Related Protein Inhibitory Effect by Treatment of HepG2 Cells with Noranhydroicaritin and Statin in Combination The cells aliquoted by the method of Example 7 were treated with noranhydroicaritin or a statin (atorvastatin or rosuvastatin) singly or with noranhydroicaritin and a statin (atorvastatin or rosuvastatin) simultaneously, and the proteins were extracted. On an SDS-polyacrylamide gel, 30 μg of each protein was electrophoresed, and attached to a membrane, and then protein expression levels were confirmed using the respective antibodies: phospho-AMPK, PCSK9, LDLR, and PPARγ.

Figure 9:
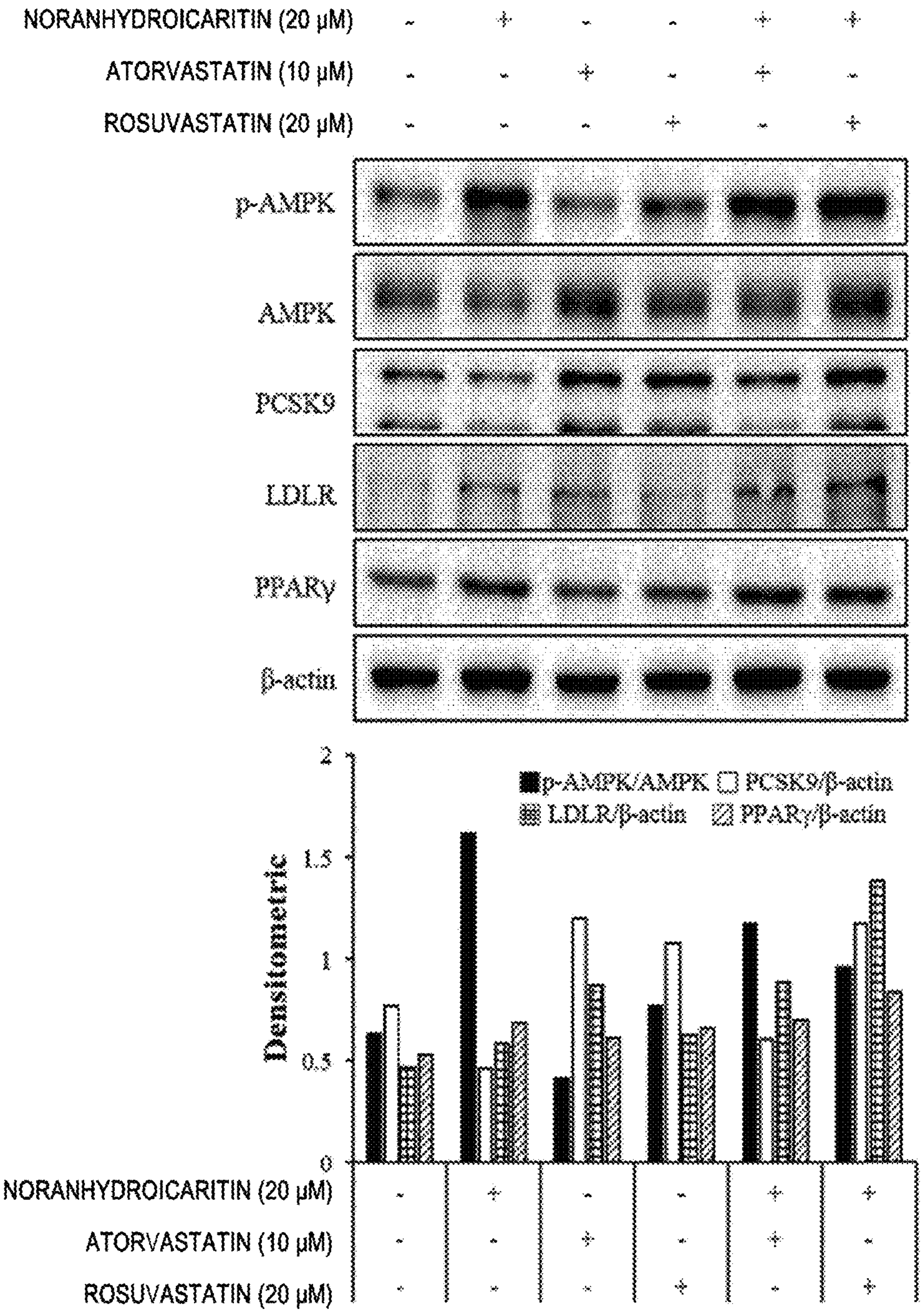
FIG. 9 illustrates changes in the expression of proteins involved in arteriosclerosis when HepG2 cells are treated with noranhydroicaritin and a statin in combination.

As a result, as can be seen from FIG. 9, it was confirmed that the quantity of PCSK9 increased when the cells were treated with each of atorvastatin and rosuvastatin singly, but the quantity of PCSK9 decreased in the cells treated with noranhydroicaritin. On the other hand, it was confirmed that the expression levels of pAMPK, LDLR, and PPARγ proteins increased in the case of treating the cells with noranhydroicaritin and a statin in combination as compared to those in the case of treating the cells with each of atorvastatin and rosuvastatin singly.

In other words, noranhydroicaritin can be used with statin-based drugs in combination to alleviate the side effects of increasing not only LDLR but also PCSK9 expression at the time of treatment with statin-based drugs. In this case, a synergistic action is acquired that the expression of pAMPK, LDLR, and PPARγ increases as compared to that in the case of treating the cells with noranhydroicaritin singly, and it can be seen that noranhydroicaritin decreases fatty acids and cholesterol in the blood and can thus be used for the prevention or treatment of cardiovascular and metabolic diseases.

Example 11: PCSK9 Inhibitory Effect by Treatment of PCSK9-Pretreated HepG2 Cells with Noranhydroicaritin and Statin in Combination The cells aliquoted by the method of Example 7 were pretreated with PCSK9 at 2 μg/mL, and then treated with noranhydroicaritin or a statin (atorvastatin or rosuvastatin) singly or with noranhydroicaritin and a statin (atorvastatin or rosuvastatin) simultaneously, and the proteins were extracted. On an SDS-polyacrylamide gel, 30 μg of each extracted protein was electrophoresed, and attached to a membrane, and then protein expression levels were confirmed using the respective antibodies: PCSK9 and LDLR. RNA was extracted and RealTime-PCR was performed to confirm the LDLR mRNA expression levels.

Figure 10:
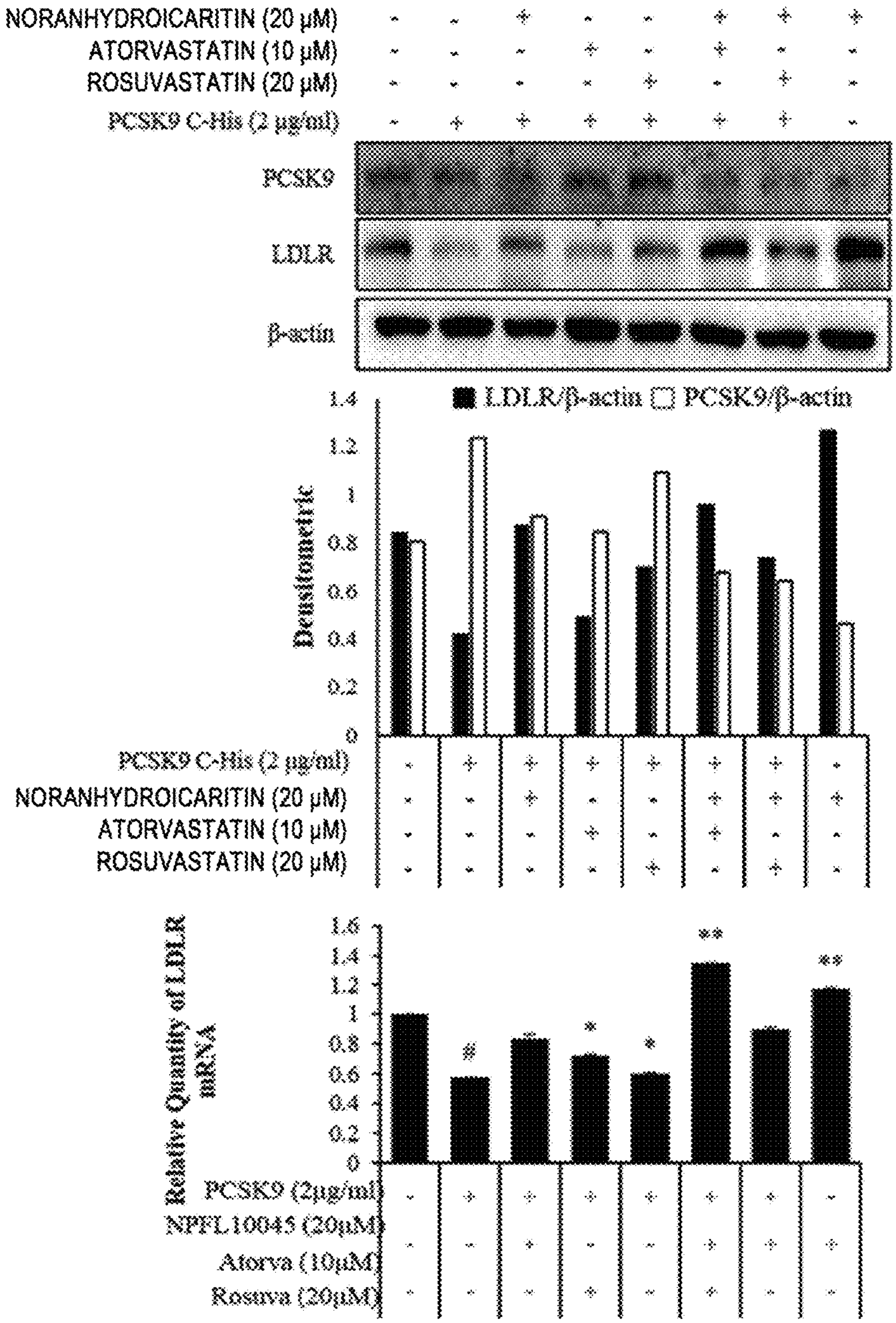
FIG. 10 illustrates changes in the expression of a protein (LDLR) involved in arteriosclerosis when PCSK9-stimulated HepG2 cells are treated with noranhydroicaritin and a statin in combination.

As a result, as can be seen from FIG. 10, it was confirmed that LDLR decreased in HepG2 cells pretreated with PCSK9. It was confirmed that LDLR expression was decreased in the cells pretreated with PCSK9 and then treated with each statin singly, but LDLR expression significantly increased in the cells pretreated with PCSK9 and then treated with noranhydroicaritin and each statin in combination. It was confirmed that the expression levels of PCSK9 actually increased in the cells pretreated with PCSK9 and then treated with each statin singly, but PCSK9 expression significantly decreased in the cells pretreated with PCSK9 and then treated with noranhydroicaritin and each statin in combination.

In other words, noranhydroicaritin can be used with statin-based drugs in combination to alleviate the side effects of increasing not only LDLR but also PCSK9 expression at the time of treatment with statin-based drugs. In this case, PCSK9 expression actually decreases as well as LDLR expression can be improved to a significant level as compared to the case of treating cells with each statin singly. As a result, noranhydroicaritin decreases fatty acids and cholesterol in the blood and can thus be used for the prevention or treatment of cardiovascular and metabolic diseases.

Example 12: Arteriosclerosis-Related Protein Expression in HepG2 Cells Treated with Noranhydroicaritin and Pitavastatin, Pravastatin, Simvastatin, or Fluvastatin in Combination The cells aliquoted by the method of Example 7 were treated with noranhydroicaritin or each statin (pravastatin, pitavastatin, fluvastatin, or simvastatin) singly or with noranhydroicaritin and a statin (pravastatin, pitavastatin, fluvastatin, or simvastatin) simultaneously, and the proteins were extracted. On an SDS-polyacrylamide gel, 30 μg of each protein was electrophoresed, and attached to a membrane, and then protein expression levels were confirmed using the respective antibodies: PCSK9 and LDLR.

Figure 11:
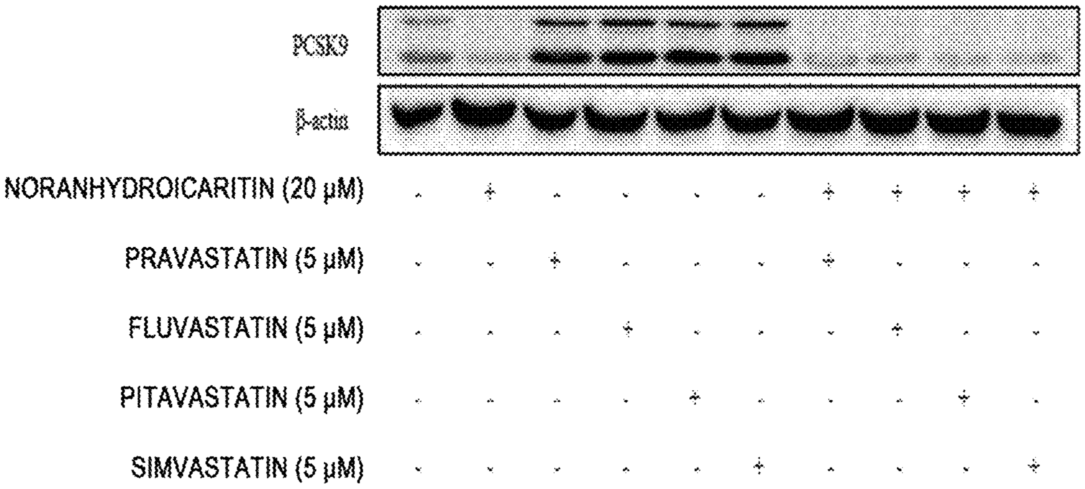
FIG. 11 illustrates changes in the expression of a protein (PCSK9) involved in arteriosclerosis when HepG2 cells are treated with noranhydroicaritin and pravastatin, pitavastatin, fluvastatin, or simvastatin in combination.

As a result, as can be seen from FIG. 11, it was confirmed that PCSK9 expression significantly decreased in the HepG2 cells treated with noranhydroicaritin and each statin in combination than in the HepG2 cells treated with each statin singly. The results converted to numerical values are presented in Table 1 below.

TABLE 1

| Simvastatin 5 μM | Pitavastatin 5 μM | Fluvastatin 5 μM | Pravastatin 5 μM | Noranhydroicaritin 20 μM | PCSK9 |
|---|---|---|---|---|---|
| − | − | − | − | − | 1 ± 0.04 |
| − | − | − | − | + | 0.34 ± 0.02 |
| − | − | − | + | − | 1.9 ± 0.06 |
| − | − | + | − | − | 1.63 ± 0.02 |
| − | + | − | − | − | 1.59 ± 0.02 |
| + | − | − | − | − | 1.85 ± 0.11 |
| − | − | − | + | + | 0.3 ± 0.02 |
| − | − | + | − | + | 0.29 ± 0.02 |
| − | + | − | − | + | 0.28 ± 0.03 |
| + | − | − | − | + | 0.24 ± 0.04 |

Figure 12:
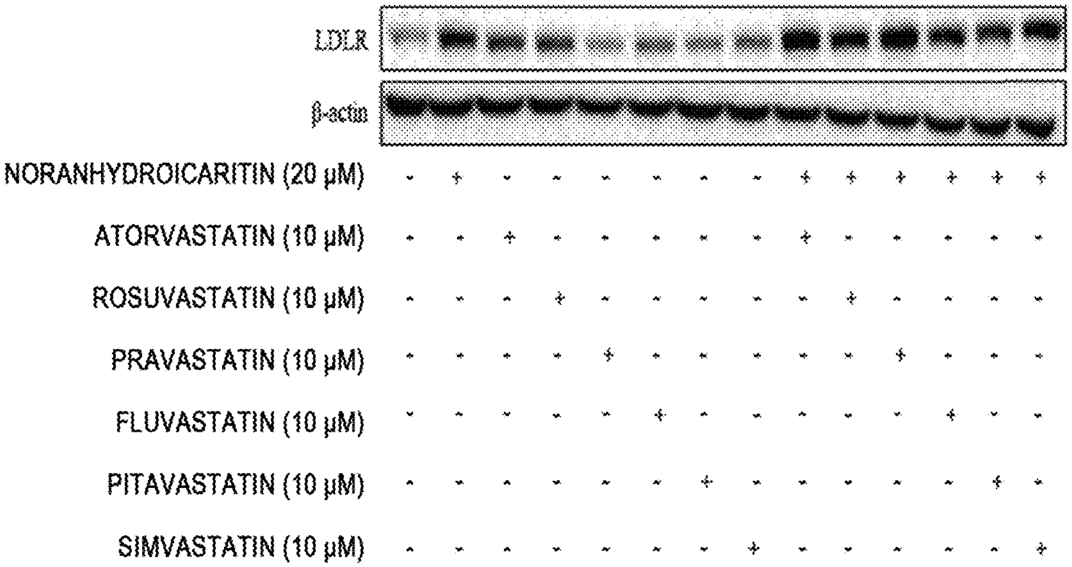
FIG. 12 illustrates changes in the expression of a protein (LDLR) involved in arteriosclerosis when HepG cells are treated with noranhydroicaritin and atorvastatin, rosuvastatin, pravastatin, pitavastatin, fluvastatin, or simvastatin in combination.

In addition, as can be seen from FIG. 12, it was confirmed that LDLR significantly increased in the cells treated with noranhydroicaritin and each statin (atorvastatin, rosuvastatin, pravastatin, pitavastatin, fluvastatin, or simvastatin) in combination than in the cells treated with each statin singly.

In other words, noranhydroicaritin can be used with statin-based drugs in combination to alleviate the side effects of increasing not only LDLR but also PCSK9 expression at the time of treatment with atorvastatin, rosuvastatin, pravastatin, pitavastatin, fluvastatin, or simvastatin of a statin-based drug. In this case, PCSK9 expression actually decreases, and also, LDLR expression can be improved to a significant level as compared to the case of treating cells with each statin singly. As a result, noranhydroicaritin decreases fatty acids and cholesterol in the blood and can thus be used for the prevention or treatment of cardiovascular and metabolic diseases.

Figure 13:
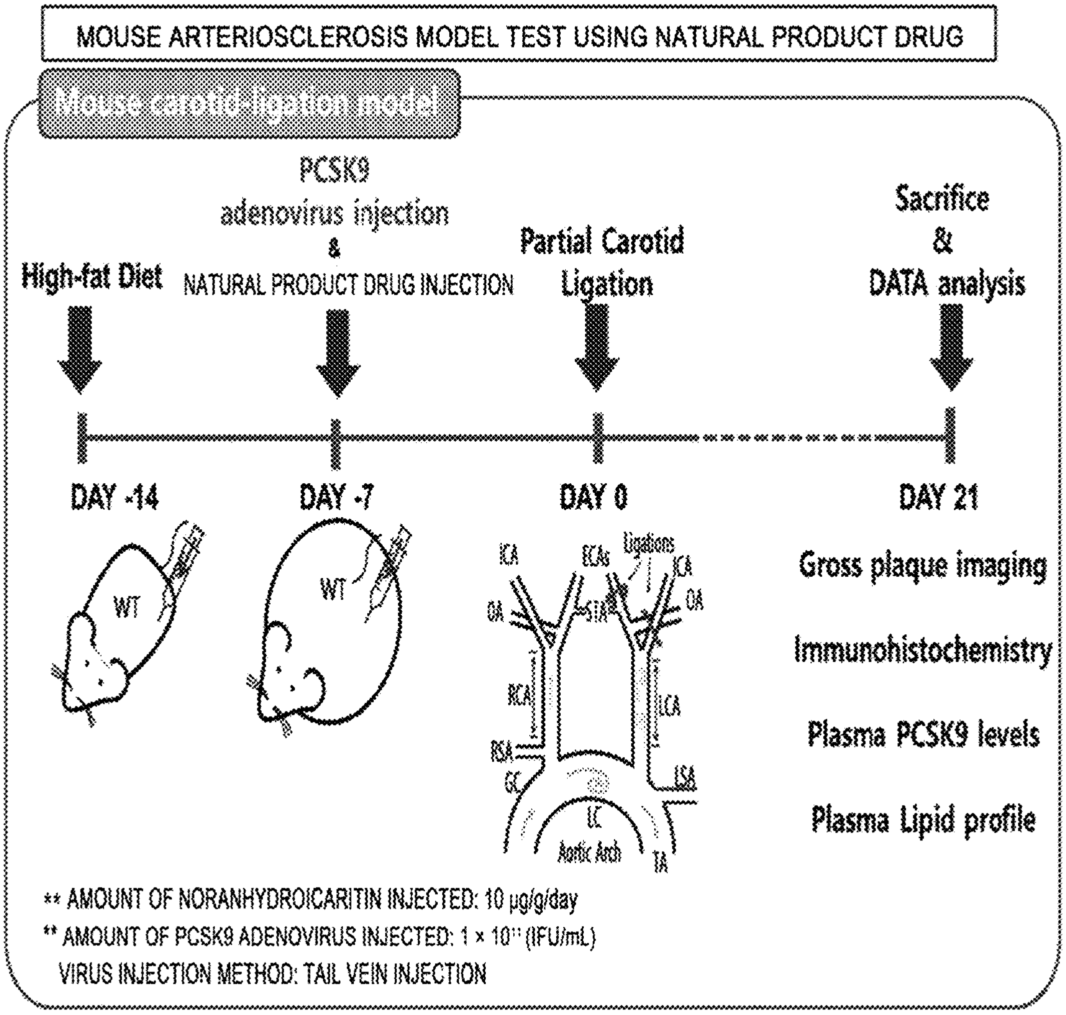
FIG. 13 illustrates a mouse arteriosclerosis model treated with PCSK9 and noranhydroicaritin.

Example 13: Arteriosclerosis Inhibitory Effect of Noranhydroicaritin in PCSK9-Injected Mouse Carotid-Ligation Model <Example 13-1> Preparation of Mouse Arteriosclerosis Model By ligation to the carotid artery of 6- to 8-week-old mice, mechanical stress was applied to induce inflammation, thrombosis, oxidative stress, and shear stress, and the function and structure of the external carotid (EC) were changed to prepare an atherosclerosis model (FIG. 13).

Specifically, ligation was performed on the left common carotid artery (LCA) after abdominal anesthesia by performing carotid artery ligation on mice fed a high-fat diet for one week. Partial ligation of three branches in the LCA, the external carotid artery (ECA), the internal carotid artery (ICA), and the occipital artery (OA) was performed. At this time, ICA and OA were ligated, and ECA was ligated separately. In mice subjected to ligation, the amount of blood flow to the heart decreased and the direction of blood flow changed, whereby an atherosclerosis model was prepared.

<Example 13-2> Confirmation of Effect by Treatment of Atherosclerosis Model Mice with Noranhydroicaritin Carotid artery ligation was performed one week after injection of AAV-PCSK9 Virus ($1\times10^{11}$ IFU/mL) and noranhydroicaritin (10 μg/g/day). After 3 weeks of ligation, it was confirmed whether the atherosclerosis model was completed, and gross plaque imaging and immunofluorescence were performed to confirm the arteriosclerosis inhibitory effect of noranhydroicaritin.

Figure 14:
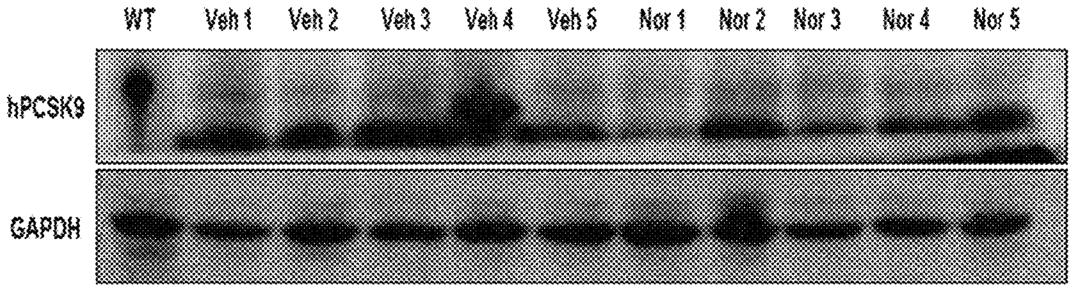
FIG. 14 illustrates the results acquired by measuring the expression levels of PCSK9 in liver tissue through western blot to confirm a mouse arteriosclerosis model.

First, it was confirmed whether the arteriosclerosis model was properly prepared through western blot, and as a result, it was confirmed that the expression of PCSK9 increased in the liver tissue of the PCSK9 virus-injected vehicles and noranhydroicaritin-treated mice than in the WT mice, as can be seen from FIG. 14.

Figure 15:
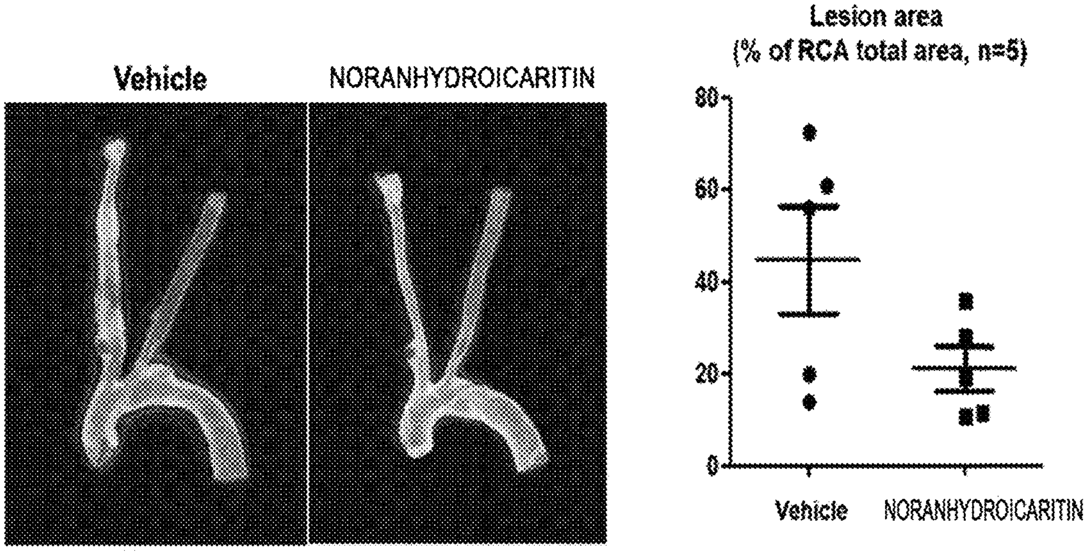
FIG. 15 illustrates the degree of recovery by noranhydroicaritin after carotid-ligation in a mouse arteriosclerosis model.

As a result of the total plaque imaging, it was confirmed that the atherosclerotic plaque-formed area significantly decreased in the noranhydroicaritin-treated group (about 20%) as compared to that in the vehicle group (about 45%), as can be seen from FIG. 15.

Furthermore, the arteriosclerosis inhibitory effect of noranhydroicaritin was confirmed using immunofluorescence. Specifically, a mouse carotid artery was obtained and fixed in 4% PFA for one day, and then prepared into a block. As the inflammatory response in blood vessels progresses, the arteriosclerosis worsens, and thus the marker F/480 of macrophages causing arteriosclerotic inflammatory response and TNF-α, IL-1B, and MCP-1, which are pro-inflammatory cytokines secreted when the inflammatory response occurs, were stained. Staining was performed using the antibody for each of CAP1(1:200), PCSK9(1:100), F4/80(1:100), TNF-α(1:100), IL-16(1:100), and MCP-1(1:100), then imaging was performed using a confocal microscope, and bioluminescence was evaluated.

Figure 16:
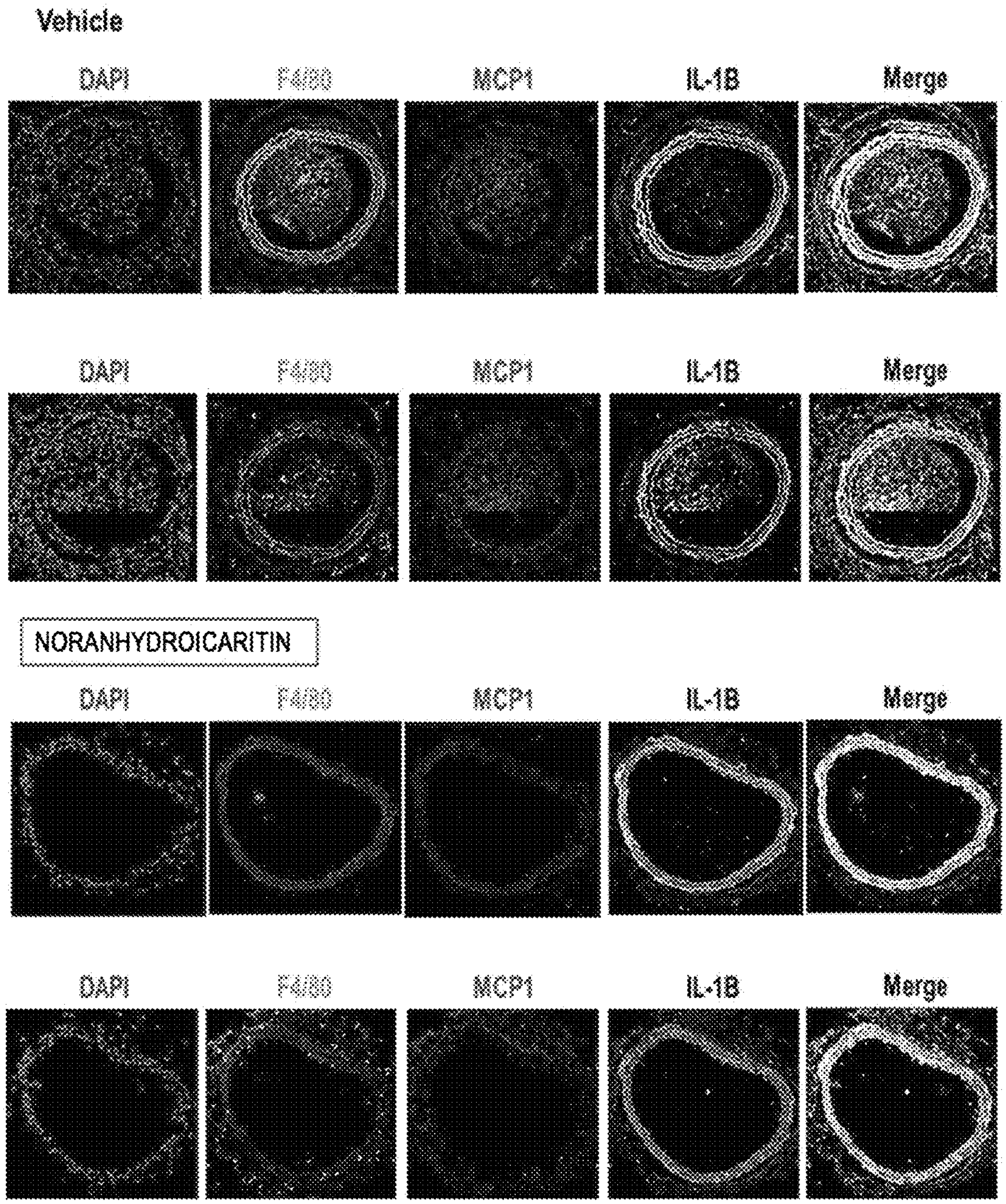
FIG. 16 illustrates the level of macrophage marker F/480, which causes an inflammatory response, and the levels of TNF-α, IL-1B, MCP-1, and PCSK9, which are pro-inflammatory cytokines secreted when an inflammatory response occurs when a mouse arteriosclerosis model is treated with noranhydroicaritin, through immunofluorescence.

As a result, as can be seen from FIG. 16, it was confirmed that the expression of pro-inflammatory markers TNF-α, IL-1B, and MCP-1 decreased in the group injected with noranhydroicaritin, and the expression of F/480, a marker of macrophages, also decreased. It was confirmed that the expression of PCSK9 also significantly decreased in the group injected with noranhydroicaritin as compared to that in the control. Consequently, noranhydroicaritin has an effect of alleviating arteriosclerosis by inhibiting the progression of inflammatory response in blood vessels, increases LDLR by decreasing PCSK9 expression, and decreases fatty acids and cholesterol in the blood, and can thus be used for the prevention or treatment of cardiovascular and metabolic diseases.

Based on the above description, those skilled in the art to which the present invention pertains will understand that the present invention may be implemented in a different specific form without changing the technical spirit or essential characteristics thereof. Therefore, it should be understood that the above embodiment is not limitative, but illustrative in all aspects. The scope of the present invention is defined by the appended claims rather than by the description preceding them, and therefore all changes and modifications that fall within metes and bounds of the claims or equivalents of such metes and bounds are therefore intended to be embraced by the claims.

The invention claimed is:

1. A method for treating cardiovascular and metabolic diseases, comprising: administering a composition comprising a noranhydroicaritin represented by a following Chemical Formula (1) or a pharmaceutically acceptable salt thereof; and a statin-based drug as an active ingredient to a subject in need thereof:

[Chem. 1]

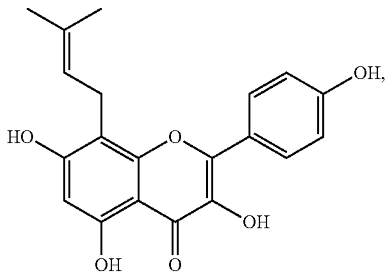

wherein the statin-based drug is atorvastatin, rosuvastatin, pitavastatin, pravastatin, simvastatin, or fluvastatin, wherein the cardiovascular and metabolic diseases is any one selected from the group consisting of dyslipidemia, coronary arteriosclerosis, and atherosclerosis, and wherein the composition alleviates side effects of concomitant increase in PCSK9 following treatment with a statin-based drug.

2. The method according to claim 1, wherein the statin-based drug exhibits HMG-COA reductase inhibitory activity.

3. A method for improving cardiovascular and metabolic diseases, comprising: administering a food composition comprising noranhydroicaritin and a statin-based drug as an active ingredient, wherein the statin-based drug is atorvastatin, rosuvastatin, pitavastatin, pravastatin, simvastatin, or fluvastatin, wherein the cardiovascular and metabolic diseases is any one selected from the group consisting of dyslipidemia, coronary arteriosclerosis, and atherosclerosis, and wherein the composition alleviates side effects of concomitant increase in PCSK9 following treatment with a statin-based drug.

* * * * *